(12) United States Patent
Hacohen

(10) Patent No.: US 9,788,941 B2
(45) Date of Patent: Oct. 17, 2017

(54) AXIALLY-SHORTENING PROSTHETIC VALVE

(71) Applicant: MITRALTECH LTD., Or Yehuda (IL)

(72) Inventor: Gil Hacohen, Ramat Gan (IL)

(73) Assignee: MITRALTECH LTD., Or Yehuda (IL)

( * ) Notice: Subject to any disclaimer, the term of this patent is extended or adjusted under 35 U.S.C. 154(b) by 0 days.

(21) Appl. No.: 14/626,267

(22) Filed: Feb. 19, 2015

(65) Prior Publication Data

US 2015/0157457 A1 Jun. 11, 2015

Related U.S. Application Data

(62) Division of application No. 13/044,694, filed on Mar. 10, 2011, now abandoned.

(Continued)

(51) Int. Cl.
*A61F 2/24* (2006.01)
*A61B 17/04* (2006.01)
(Continued)

(52) U.S. Cl.
CPC ........ *A61F 2/2418* (2013.01); *A61B 17/0401* (2013.01); *A61B 17/064* (2013.01); *A61F 2/2409* (2013.01); *A61F 2/2427* (2013.01); *A61F 2/2436* (2013.01); *A61F 2/2457* (2013.01); *A61B 2017/00243* (2013.01); *A61B 2017/0414* (2013.01);
(Continued)

(58) Field of Classification Search
CPC ........ A61F 2/24; A61F 2/2409; A61F 2/2412; A61F 2/2418

USPC .................................................. 623/2.1–2.19
See application file for complete search history.

(56) References Cited

U.S. PATENT DOCUMENTS

| 5,405,378 A | 4/1995 | Strecker |
| 5,443,500 A | 8/1995 | Sigwart |

(Continued)

FOREIGN PATENT DOCUMENTS

| WO | 2006/070372 A2 | 7/2006 |
| WO | 2006/089236 A1 | 8/2006 |

(Continued)

OTHER PUBLICATIONS

USPTO RR dated Jan. 20, 2016 in connection with U.S. Appl. No. 14/161,921.

(Continued)

*Primary Examiner* — Jacqueline Wozniki
(74) *Attorney, Agent, or Firm* — Ladas & Parry LLP

(57) ABSTRACT

Apparatus and methods are described including a prosthetic atrioventricular valve (10) for coupling to a native atrioventricular valve (12). The prosthetic valve includes a support frame (20) and a covering (22), which at least partially covers the support frame. The support frame and the covering are shaped so as to define a downstream skirt (24). A plurality of prosthetic leaflets (40) are coupled to at least one element selected from the group consisting of: the support frame and the covering. An elongated anchoring member (152) is positioned around the downstream skirt in a subvalvular space (150), such that the anchoring member presses native leaflets (30) of the native valve against the downstream skirt, thereby anchoring the prosthetic valve to the native valve. Other applications are also described.

11 Claims, 16 Drawing Sheets

Related U.S. Application Data

(60) Provisional application No. 61/312,412, filed on Mar. 10, 2010.

(51) Int. Cl.
*A61B 17/064* (2006.01)
*A61B 17/00* (2006.01)

(52) U.S. Cl.
CPC .............. *A61B 2017/0441* (2013.01); *A61B 2017/0464* (2013.01); *A61B 2017/0649* (2013.01); *A61F 2220/0016* (2013.01); *A61F 2230/005* (2013.01); *A61F 2230/0054* (2013.01); *A61F 2230/0078* (2013.01); *A61F 2250/0063* (2013.01)

(56) References Cited

U.S. PATENT DOCUMENTS

| | | | |
|---|---|---|---|
| 5,647,857 A | 7/1997 | Anderson et al. | |
| 5,765,682 A | 6/1998 | Bley et al. | |
| 5,873,906 A | 2/1999 | Lau et al. | |
| 5,980,565 A | 11/1999 | Jayaraman | |
| 6,019,787 A | 2/2000 | Richard et al. | |
| 6,165,210 A | 12/2000 | Lau et al. | |
| 6,193,745 B1 | 2/2001 | Fogarty et al. | |
| 6,334,873 B1 | 1/2002 | Lane et al. | |
| 6,350,278 B1 | 2/2002 | Lenker et al. | |
| 6,352,561 B1 | 3/2002 | Leopold et al. | |
| 6,454,799 B1 | 9/2002 | Schreck | |
| 6,458,153 B1 * | 10/2002 | Bailey | A61F 2/2418 623/1.24 |
| 6,551,350 B1 | 4/2003 | Thornton et al. | |
| 6,558,396 B1 | 5/2003 | Inoue | |
| 6,767,362 B2 | 7/2004 | Schreck | |
| 6,821,297 B2 | 11/2004 | Snyders | |
| 7,018,406 B2 * | 3/2006 | Seguin | A61F 2/2418 606/194 |
| 7,101,396 B2 | 9/2006 | Artof et al. | |
| 7,137,184 B2 | 11/2006 | Schreck | |
| 7,201,772 B2 * | 4/2007 | Schwammenthal | A61F 2/2418 623/1.24 |
| 7,329,279 B2 | 2/2008 | Haug et al. | |
| 7,374,573 B2 | 5/2008 | Gabbay | |
| 7,377,938 B2 | 5/2008 | Sarac et al. | |
| 7,429,269 B2 * | 9/2008 | Schwammenthal | A61F 2/24 623/2.14 |
| 7,510,575 B2 | 3/2009 | Spenser et al. | |
| 7,585,321 B2 * | 9/2009 | Cribier | A61F 2/2412 623/2.14 |
| 7,625,403 B2 | 12/2009 | Krivoruchko | |
| 7,648,528 B2 | 1/2010 | Styrc | |
| 7,682,380 B2 | 3/2010 | Thornton et al. | |
| 7,717,952 B2 | 5/2010 | Case et al. | |
| 7,748,389 B2 | 7/2010 | Salahieh et al. | |
| 7,758,632 B2 | 7/2010 | Hojeibane et al. | |
| 7,780,726 B2 | 8/2010 | Seguin | |
| 7,837,727 B2 * | 11/2010 | Goetz | A61F 2/2418 623/1.15 |
| 7,942,927 B2 | 5/2011 | Kaye et al. | |
| 7,955,377 B2 | 6/2011 | Melsheimer | |
| 7,959,672 B2 | 6/2011 | Salahieh et al. | |
| 8,002,826 B2 | 8/2011 | Seguin | |
| 8,016,882 B2 | 9/2011 | Macoviak et al. | |
| 8,048,138 B2 | 11/2011 | Sullivan et al. | |
| 8,048,153 B2 * | 11/2011 | Salahieh | A61F 2/2418 623/2.11 |
| 8,062,355 B2 * | 11/2011 | Figulla | A61F 2/2418 623/1.24 |
| 8,070,802 B2 * | 12/2011 | Lamphere | A61F 2/2418 623/1.26 |
| 8,092,520 B2 | 1/2012 | Quadri | |
| 8,109,996 B2 | 2/2012 | Stacchino et al. | |
| 8,118,866 B2 * | 2/2012 | Herrmann | A61F 2/2412 623/2.11 |
| 8,142,492 B2 | 3/2012 | Forster et al. | |
| 8,142,496 B2 * | 3/2012 | Berreklouw | A61B 17/11 623/2.36 |
| 8,163,008 B2 | 4/2012 | Wilson et al. | |
| 8,172,898 B2 | 5/2012 | Alferness et al. | |
| 8,182,528 B2 * | 5/2012 | Salahieh | A61F 2/2418 623/2.11 |
| 8,216,301 B2 | 7/2012 | Bonhoeffer et al. | |
| 8,267,988 B2 | 9/2012 | Hamer et al. | |
| 8,303,653 B2 | 11/2012 | Bonhoeffer et al. | |
| 8,337,541 B2 | 12/2012 | Quadri et al. | |
| 8,343,213 B2 | 1/2013 | Salahieh et al. | |
| 8,366,767 B2 | 2/2013 | Zhang | |
| 8,403,981 B2 | 3/2013 | Forster et al. | |
| 8,403,983 B2 | 3/2013 | Quadri et al. | |
| 8,408,214 B2 | 4/2013 | Spenser | |
| 8,414,644 B2 | 4/2013 | Quadri et al. | |
| 8,425,593 B2 | 4/2013 | Braido et al. | |
| 8,444,689 B2 | 5/2013 | Zhang | |
| 8,449,599 B2 | 5/2013 | Chau et al. | |
| 8,454,686 B2 | 6/2013 | Alkhatib | |
| 8,540,767 B2 | 9/2013 | Zhang | |
| 8,545,544 B2 | 10/2013 | Spenser et al. | |
| 8,551,161 B2 | 10/2013 | Dolan | |
| 8,562,672 B2 | 10/2013 | Bonhoeffer et al. | |
| 8,579,964 B2 | 11/2013 | Lane et al. | |
| 8,579,965 B2 | 11/2013 | Bonhoeffer et al. | |
| 8,585,755 B2 | 11/2013 | Chau et al. | |
| 8,585,756 B2 | 11/2013 | Bonhoeffer et al. | |
| 8,591,570 B2 | 11/2013 | Revuelta et al. | |
| 8,623,075 B2 | 1/2014 | Murray, III et al. | |
| 8,628,569 B2 | 1/2014 | Benichou et al. | |
| 8,628,570 B2 | 1/2014 | Seguin | |
| 8,652,203 B2 | 2/2014 | Quadri et al. | |
| 8,679,174 B2 | 3/2014 | Ottma et al. | |
| 8,685,086 B2 | 4/2014 | Navia et al. | |
| 8,728,155 B2 | 5/2014 | Montorfano et al. | |
| 8,747,460 B2 | 6/2014 | Tuval et al. | |
| 8,771,345 B2 | 7/2014 | Tuval et al. | |
| 8,784,472 B2 | 7/2014 | Eidenschink | |
| 8,784,481 B2 | 7/2014 | Alkhatib et al. | |
| 8,795,355 B2 | 8/2014 | Alkhatib | |
| 8,795,356 B2 | 8/2014 | Quadri et al. | |
| 8,795,357 B2 | 8/2014 | Yohanan et al. | |
| 8,808,366 B2 | 8/2014 | Braido et al. | |
| 8,840,664 B2 | 9/2014 | Karapetian et al. | |
| 8,852,261 B2 | 10/2014 | White | |
| 8,852,272 B2 * | 10/2014 | Gross | A61F 2/2436 623/1.26 |
| 8,870,948 B1 | 10/2014 | Erzberger et al. | |
| 8,870,949 B2 | 10/2014 | Rowe | |
| 8,894,702 B2 | 11/2014 | Quadri et al. | |
| 8,906,083 B2 | 12/2014 | Obermiller et al. | |
| 8,911,455 B2 | 12/2014 | Quadri et al. | |
| 8,911,489 B2 | 12/2014 | Ben-Muvhar | |
| 8,932,343 B2 | 1/2015 | Alkhatib et al. | |
| 8,961,595 B2 | 2/2015 | Alkhatib | |
| 8,979,922 B2 | 3/2015 | Jayasinghe | |
| 8,986,373 B2 | 3/2015 | Chau et al. | |
| 8,992,608 B2 | 3/2015 | Haug et al. | |
| 8,998,982 B2 | 4/2015 | Richter et al. | |
| 9,005,273 B2 | 4/2015 | Salahieh et al. | |
| 9,023,100 B2 | 5/2015 | Quadri et al. | |
| 9,034,032 B2 * | 5/2015 | McLean | A61F 2/2409 623/2.12 |
| 9,034,033 B2 * | 5/2015 | McLean | A61F 2/2409 623/2.12 |
| 9,039,757 B2 * | 5/2015 | McLean | A61F 2/2409 623/1.24 |
| 9,050,188 B2 | 6/2015 | Schweich, Jr. et al. | |
| 9,072,603 B2 | 7/2015 | Tuval et al. | |
| 9,084,676 B2 | 7/2015 | Chau et al. | |
| 9,125,738 B2 | 9/2015 | Figulla et al. | |
| 9,125,740 B2 | 9/2015 | Morriss et al. | |
| 9,132,006 B2 | 9/2015 | Spenser et al. | |
| 9,138,312 B2 | 9/2015 | Tuval et al. | |
| 9,173,738 B2 | 11/2015 | Murray, III et al. | |
| 9,220,594 B2 | 12/2015 | Braido et al. | |
| 9,226,820 B2 | 1/2016 | Braido et al. | |

(56) References Cited

U.S. PATENT DOCUMENTS

| | | |
|---|---|---|
| 9,226,839 B1 | 1/2016 | Kariniemi et al. |
| 9,232,995 B2 | 1/2016 | Kovalsky et al. |
| 9,241,791 B2 | 1/2016 | Braido et al. |
| 9,241,794 B2 | 1/2016 | Braido et al. |
| 9,248,014 B2 | 2/2016 | Lane et al. |
| 9,289,290 B2 | 3/2016 | Alkhatib et al. |
| 9,289,291 B2 | 3/2016 | Gorman, III et al. |
| 9,295,550 B2 | 3/2016 | Nguyen et al. |
| 9,295,552 B2 | 3/2016 | McLean et al. |
| 9,301,836 B2 | 4/2016 | Buchbinder et al. |
| D755,384 S | 5/2016 | Pesce et al. |
| 9,326,852 B2 | 5/2016 | Spenser |
| 9,421,098 B2 | 8/2016 | Gifford, III et al. |
| 9,427,316 B2 | 8/2016 | Schweich, Jr. et al. |
| 9,532,870 B2 | 1/2017 | Cooper et al. |
| 2001/0056295 A1 | 12/2001 | Solem |
| 2002/0099436 A1 | 7/2002 | Thornton et al. |
| 2004/0122503 A1 | 6/2004 | Campbell et al. |
| 2004/0143315 A1 | 7/2004 | Bruun et al. |
| 2004/0249433 A1 | 12/2004 | Freitag |
| 2004/0260394 A1 | 12/2004 | Douk et al. |
| 2005/0038494 A1 | 2/2005 | Eidenschink |
| 2005/0080430 A1 | 4/2005 | Wright, Jr. et al. |
| 2005/0137688 A1 | 6/2005 | Salahieh et al. |
| 2005/0137689 A1 | 6/2005 | Salahieh et al. |
| 2005/0137695 A1 | 6/2005 | Salahieh et al. |
| 2005/0143809 A1 | 6/2005 | Salahieh et al. |
| 2005/0154443 A1 | 7/2005 | Linder et al. |
| 2005/0240200 A1 | 10/2005 | Bergheim |
| 2006/0015171 A1 | 1/2006 | Armstrong |
| 2006/0020333 A1 | 1/2006 | Lashinski et al. |
| 2006/0089627 A1 | 4/2006 | Burnett et al. |
| 2006/0178700 A1 | 8/2006 | Quinn |
| 2006/0195183 A1 | 8/2006 | Navia et al. |
| 2006/0212111 A1 | 9/2006 | Case et al. |
| 2006/0259137 A1 | 11/2006 | Artof et al. |
| 2006/0271166 A1 | 11/2006 | Thill et al. |
| 2007/0055340 A1 | 3/2007 | Pryor |
| 2007/0198077 A1 | 8/2007 | Cully et al. |
| 2007/0213813 A1 | 9/2007 | Von Segesser et al. |
| 2008/0071363 A1 | 3/2008 | Tuval et al. |
| 2008/0071369 A1 | 3/2008 | Tuval et al. |
| 2008/0082083 A1 | 4/2008 | Forde et al. |
| 2008/0097595 A1 | 4/2008 | Gabbay |
| 2008/0140003 A1 | 6/2008 | Bei et al. |
| 2008/0167705 A1 | 7/2008 | Agnew |
| 2008/0234814 A1* | 9/2008 | Salahieh ............... A61F 2/2418 623/2.11 |
| 2008/0255580 A1 | 10/2008 | Hoffman et al. |
| 2008/0294234 A1 | 11/2008 | Hartley et al. |
| 2009/0005863 A1 | 1/2009 | Goetz et al. |
| 2009/0054969 A1 | 2/2009 | Salahieh et al. |
| 2009/0112159 A1 | 4/2009 | Slattery et al. |
| 2009/0299449 A1 | 12/2009 | Styrc |
| 2009/0306768 A1 | 12/2009 | Quadri |
| 2010/0076548 A1 | 3/2010 | Konno |
| 2010/0131054 A1 | 5/2010 | Tuval et al. |
| 2010/0137979 A1 | 6/2010 | Tuval et al. |
| 2010/0161036 A1 | 6/2010 | Pintor et al. |
| 2010/0161042 A1 | 6/2010 | Maisano et al. |
| 2010/0179649 A1 | 7/2010 | Richter et al. |
| 2010/0234940 A1 | 9/2010 | Dolan |
| 2011/0071626 A1 | 3/2011 | Wright et al. |
| 2011/0077730 A1 | 3/2011 | Fentster |
| 2011/0098525 A1* | 4/2011 | Kermode ......... A61B 17/12122 600/37 |
| 2011/0137397 A1 | 6/2011 | Chau et al. |
| 2011/0208283 A1 | 8/2011 | Rust |
| 2011/0208298 A1 | 8/2011 | Tuval et al. |
| 2011/0218619 A1 | 9/2011 | Benichou et al. |
| 2011/0224785 A1 | 9/2011 | Hacohen |
| 2011/0282439 A1 | 11/2011 | Thill et al. |
| 2011/0319989 A1 | 12/2011 | Lane et al. |
| 2012/0022633 A1 | 1/2012 | Olson et al. |
| 2012/0078357 A1 | 3/2012 | Conklin |
| 2012/0101572 A1 | 4/2012 | Kovalsky et al. |
| 2012/0123511 A1 | 5/2012 | Brown |
| 2012/0130473 A1 | 5/2012 | Norris et al. |
| 2012/0130474 A1 | 5/2012 | Buckley |
| 2012/0130475 A1 | 5/2012 | Shaw |
| 2012/0165915 A1 | 6/2012 | Melsheimer et al. |
| 2012/0179244 A1 | 7/2012 | Schankereli et al. |
| 2012/0296360 A1 | 11/2012 | Norris et al. |
| 2012/0310328 A1 | 12/2012 | Olson et al. |
| 2012/0330408 A1 | 12/2012 | Hillukka et al. |
| 2013/0006347 A1 | 1/2013 | McHugo |
| 2013/0018450 A1 | 1/2013 | Hunt |
| 2013/0041451 A1 | 2/2013 | Patterson et al. |
| 2013/0123896 A1 | 5/2013 | Bloss et al. |
| 2013/0123900 A1 | 5/2013 | Eblacas et al. |
| 2013/0150945 A1 | 6/2013 | Crawford et al. |
| 2013/0150956 A1 | 6/2013 | Yohanan et al. |
| 2013/0158647 A1 | 6/2013 | Norris et al. |
| 2013/0166017 A1 | 6/2013 | Cartledge et al. |
| 2013/0166022 A1 | 6/2013 | Conklin |
| 2013/0172978 A1 | 7/2013 | Vidlund et al. |
| 2013/0211501 A1 | 8/2013 | Buckley et al. |
| 2013/0245742 A1 | 9/2013 | Norris |
| 2013/0297013 A1 | 11/2013 | Klima et al. |
| 2013/0310928 A1* | 11/2013 | Morriss ............... A61F 2/2418 623/2.12 |
| 2013/0325114 A1 | 12/2013 | McLean et al. |
| 2013/0331929 A1 | 12/2013 | Mitra et al. |
| 2014/0005778 A1* | 1/2014 | Buchbinder .......... A61F 2/2445 623/2.18 |
| 2014/0018911 A1 | 1/2014 | Zhou et al. |
| 2014/0031928 A1 | 1/2014 | Murphy et al. |
| 2014/0046430 A1 | 2/2014 | Shaw |
| 2014/0081376 A1 | 3/2014 | Burkart et al. |
| 2014/0106951 A1 | 4/2014 | Brandon |
| 2014/0120287 A1 | 5/2014 | Jacoby et al. |
| 2014/0121763 A1 | 5/2014 | Duffy et al. |
| 2014/0135894 A1 | 5/2014 | Norris et al. |
| 2014/0135895 A1 | 5/2014 | Andress et al. |
| 2014/0142681 A1 | 5/2014 | Norris |
| 2014/0148891 A1 | 5/2014 | Johnson |
| 2014/0163690 A1 | 6/2014 | White |
| 2014/0172069 A1 | 6/2014 | Roeder et al. |
| 2014/0188210 A1 | 7/2014 | Beard et al. |
| 2014/0188221 A1 | 7/2014 | Chung et al. |
| 2014/0194983 A1 | 7/2014 | Kovalsky et al. |
| 2014/0207231 A1 | 7/2014 | Hacohen et al. |
| 2014/0214159 A1 | 7/2014 | Vidlund et al. |
| 2014/0222163 A1 | 8/2014 | Xu et al. |
| 2014/0249622 A1 | 9/2014 | Carmi et al. |
| 2014/0257467 A1 | 9/2014 | Lane et al. |
| 2014/0257475 A1* | 9/2014 | Gross .................. A61F 2/2439 623/2.38 |
| 2014/0257476 A1 | 9/2014 | Montorfano et al. |
| 2014/0277358 A1 | 9/2014 | Slazas |
| 2014/0277409 A1 | 9/2014 | Bortlein et al. |
| 2014/0277427 A1 | 9/2014 | Ratz et al. |
| 2014/0296962 A1 | 10/2014 | Cartledge et al. |
| 2014/0324164 A1 | 10/2014 | Gross et al. |
| 2014/0343670 A1* | 11/2014 | Bakis .................. A61F 2/2436 623/2.11 |
| 2014/0358224 A1 | 12/2014 | Tegels et al. |
| 2014/0379065 A1 | 12/2014 | Johnson et al. |
| 2014/0379074 A1 | 12/2014 | Spence et al. |
| 2014/0379076 A1 | 12/2014 | Vidlund et al. |
| 2015/0045881 A1 | 2/2015 | Lim |
| 2015/0094802 A1* | 4/2015 | Buchbinder .......... A61F 2/2454 623/2.18 |
| 2015/0127097 A1 | 5/2015 | Neumann et al. |
| 2015/0142103 A1 | 5/2015 | Vidlund |
| 2015/0164640 A1 | 6/2015 | McLean et al. |
| 2015/0173896 A1 | 6/2015 | Richter et al. |
| 2015/0173897 A1* | 6/2015 | Raanani .............. A61F 2/2418 623/2.11 |
| 2015/0272730 A1 | 10/2015 | Melnick et al. |
| 2015/0327994 A1* | 11/2015 | Morriss ............... A61F 2/2445 623/2.17 |
| 2015/0328000 A1 | 11/2015 | Ratz et al. |
| 2016/0095700 A1 | 4/2016 | Righini |

(56) References Cited

U.S. PATENT DOCUMENTS

| | | |
|---|---|---|
| 2016/0106539 A1 | 4/2016 | Buchbinder et al. |
| 2016/0220367 A1 | 8/2016 | Barrett |
| 2016/0242902 A1 | 8/2016 | Morriss et al. |
| 2016/0310268 A1 | 10/2016 | Oba et al. |
| 2016/0324640 A1 | 11/2016 | Gifford, III et al. |

FOREIGN PATENT DOCUMENTS

| | | | |
|---|---|---|---|
| WO | 2007/059252 | A1 | 5/2007 |
| WO | 2008/029296 | A2 | 3/2008 |
| WO | 2008/070797 | A2 | 6/2008 |
| WO | 2008/103722 | A2 | 8/2008 |
| WO | 2009/091509 | A1 | 7/2009 |
| WO | 2012/024428 | A2 | 2/2012 |
| WO | 2012177942 | A2 | 12/2012 |
| WO | 2013/059747 | A1 | 4/2013 |
| WO | 2013/078497 | A1 | 6/2013 |
| WO | 2014/022124 | A1 | 2/2014 |
| WO | 2014/145338 | A1 | 9/2014 |
| WO | 2014/164364 | A1 | 10/2014 |
| WO | 2015/173794 | A1 | 11/2015 |
| WO | 2016/093877 | A1 | 6/2016 |

OTHER PUBLICATIONS

USPTO NFOA dated Dec. 10, 2015 in connection with U.S. Appl. No. 14/237,258.
USPTO NFOA dated Jan. 21, 2016 in connection with U.S. Appl. No. 14/237,264.
Francesco Maisano, MD, FESC; Valtech Cardiovalve: Novel Design Feature and Clinical Update; CRF Cardiovascular Research Foundation; TCT2015; 10 pages.
An International Search Report and Written Opinion both dated Oct. 19, 2015, PCT/IL2015/050792.
USPTO NFOA dated Jun. 30, 2015 in connection with U.S. Appl. No. 14/522,987.
U.S. Appl. No. 61/312,412, filed Mar. 10, 2010.
International Search Report and Written Opinion both dated May 30, 2016; PCT/IL2016/050125.
USPTO NFOA dated Jul. 1, 2016 in connection with U.S. Appl. No. 14/161,921.
USPTO RR dated Sep. 26, 2016 in connection with U.S. Appl. No. 14/763,004.
Saturn Project—a novel solution for transcatheter heart valve replacement specifically designed to address clinical therapeutic needs on mitral valve; Dec. 2016.
Righini presentation EuroPCR May 2015 (Saturn)—(downloaded from; https://www.pcronline.com/Cases-resourcesimages/Resources/Course-videos-slides/2015/Cardiovascularinnovation-pipeline-Mitral-and-triscupid-valve-interventions.).
EPO Office Action dated Feb. 10, 2017; Appln. 12 821 522.5-1651.
UK Office Action dated Feb. 8, 2017; UK Appln. 1613219.3.
USPTO NFOA dated Feb. 7, 2017 in connection with U.S. Appl. No. 14/689,608.

* cited by examiner

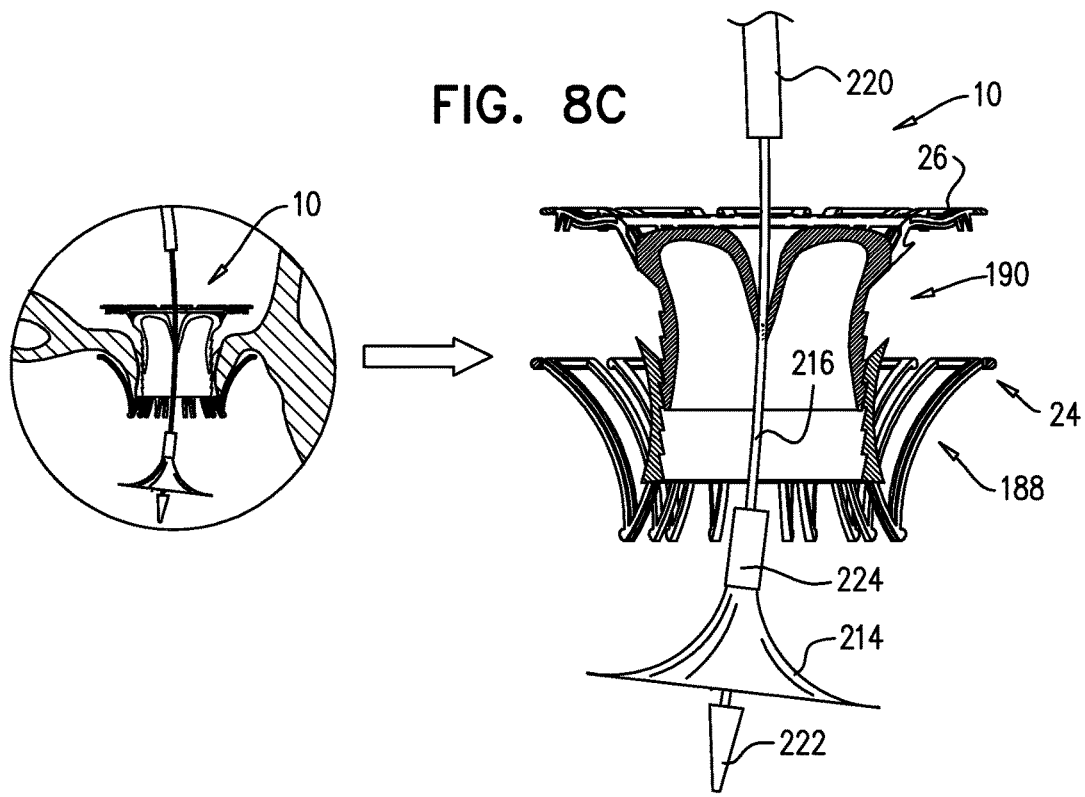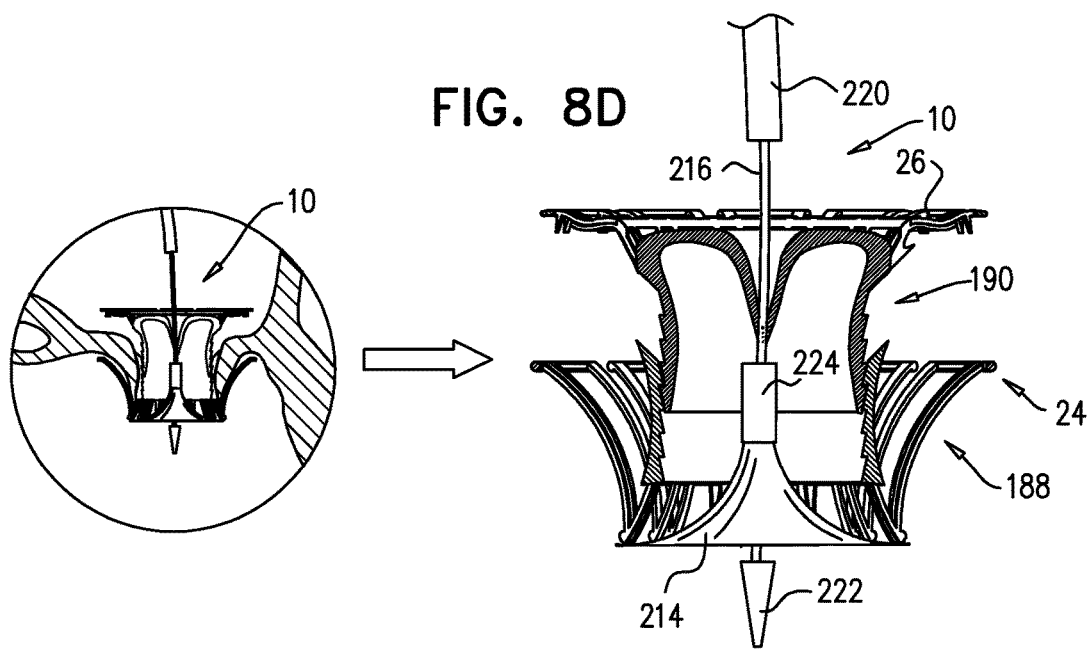

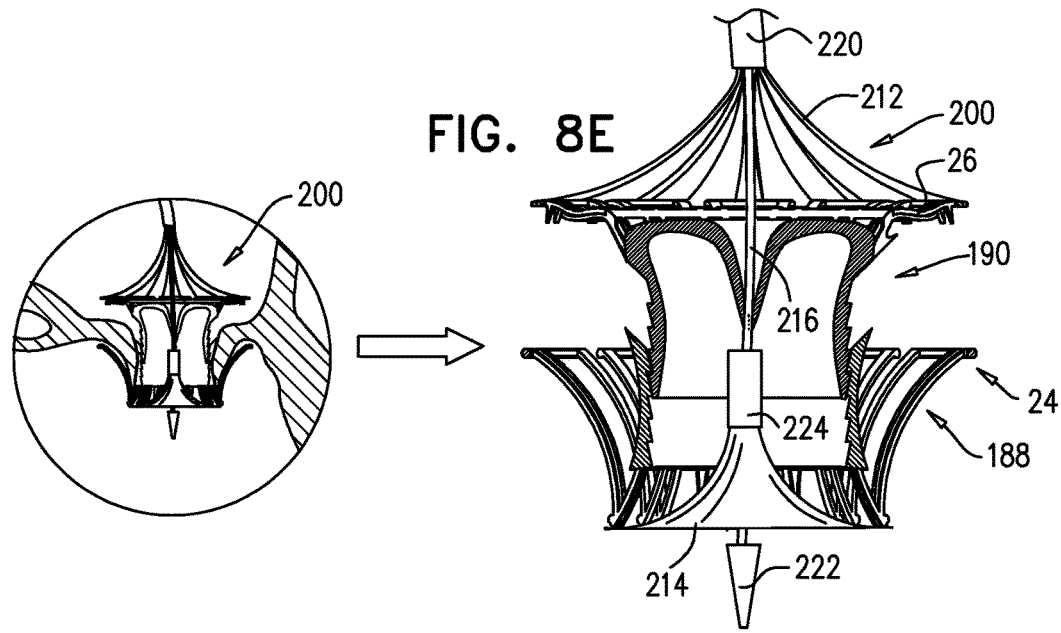
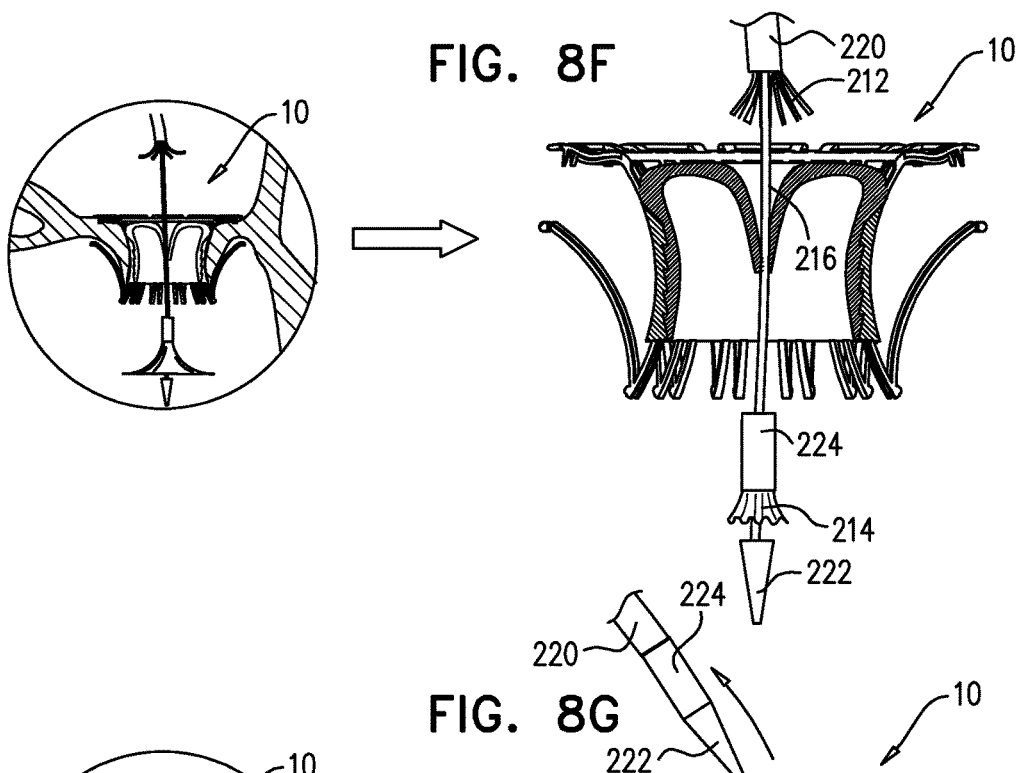
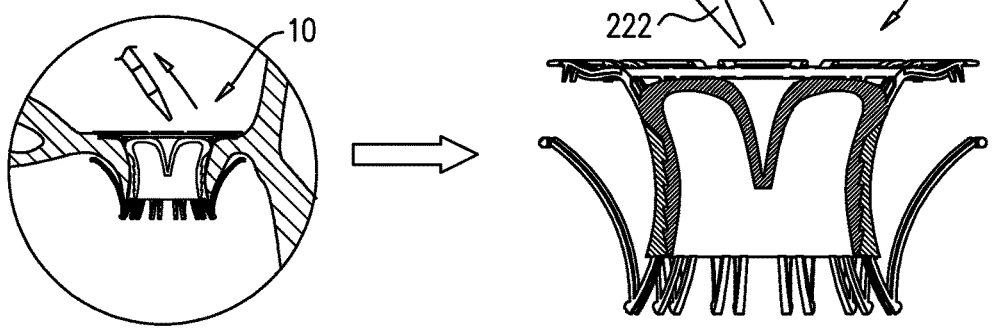

AXIALLY-SHORTENING PROSTHETIC VALVE

CROSS-REFERENCE TO RELATED APPLICATIONS

The present application is a divisional application of U.S. patent application Ser. No. 13/044,694 to Hacohen, filed on Mar. 10, 2011, entitled "Prosthetic mitral valve with tissue anchors," which published as US 2011/0224785, and which claims priority from U.S. Provisional Application 61/312,412, filed Mar. 10, 2010, entitled, "Prosthetic mitral valve with tissue anchors," which is assigned to the assignee of the present application and is incorporated herein by reference.

The present application is related to an international patent application entitled, "Prosthetic mitral valve with tissue anchors," filed on even date herewith, which published as WO 2011/111047, and which is assigned to the assignee of the present application and is incorporated herein by reference.

FIELD OF EMBODIMENTS OF THE INVENTION

Embodiments of the present invention relate in general to valve replacement. More specifically, embodiments of the present invention relate to prosthetic valves for minimally-invasive replacement of an atrioventricular valve.

BACKGROUND

Ischemic heart disease causes regurgitation of a heart valve by the combination of ischemic dysfunction of the papillary muscles, and the dilatation of the ventricle that is present in ischemic heart disease, with the subsequent displacement of the papillary muscles and the dilatation of the valve annulus.

Dilation of the annulus of the valve prevents the valve leaflets from fully coapting when the valve is closed. Regurgitation of blood from the ventricle into the atrium results in increased total stroke volume and decreased cardiac output, and ultimate weakening of the ventricle secondary to a volume overload and a pressure overload of the atrium.

SUMMARY OF APPLICATIONS

For some applications of the present invention, a collapsible prosthetic valve is configured for implantation in and/or at least partial replacement of a native atrioventricular valve of a patient, such as a native mitral valve or a native tricuspid valve. The prosthetic valve is configured to assume a collapsed state for minimally-invasive delivery to the diseased native valve, such as by percutaneous or transluminal delivery using one or more catheters. The prosthetic valve comprises a collapsible flexible support, which is at least partially covered by a covering. The prosthetic valve is shaped so as to define a downstream skirt and an upstream annular skirt. The downstream skirt is configured to be placed at the native valve, such that the downstream skirt passes through the orifice of the native valve and extends towards, and, typically partially into, a ventricle. The downstream skirt typically pushes aside and presses against the native leaflets of the native valve, which are typically left in place during and after implantation of the prosthetic valve. The upstream annular skirt is configured to be placed around a native annulus of the native valve, and to extend at least partially into an atrium such that annular skirt rests against the native annulus.

There is therefore provided, in accordance with some applications of the present invention, apparatus including a prosthetic atrioventricular valve for coupling to a native atrioventricular valve, the prosthetic valve including:
a support frame;
a covering, which at least partially covers the support frame, the support frame and the covering being shaped so as to define a downstream skirt;
a plurality of prosthetic leaflets, coupled to at least one element selected from the group consisting of: the support frame and the covering; and
an elongated anchoring member, configured to be positioned around the downstream skirt in a subvalvular space, such that the anchoring member presses native leaflets of the native valve against the downstream skirt, thereby anchoring the prosthetic valve to the native valve.

For some applications, the elongated anchoring member is configured to be positioned completely around the downstream skirt.

For some applications, the prosthetic valve further includes a contracting housing shaped so as to define a channel therethrough, a first end of the anchoring member is fixed to the contracting housing, and a second end of the anchoring member passes through the channel.

For some applications, the prosthetic valve is configured to assume collapsed and expanded states.

There is further provided, in accordance with some applications of the present invention, apparatus including a prosthetic atrioventricular valve for coupling to a native atrioventricular valve, the prosthetic valve including:
a support frame;
a covering, which at least partially covers the support frame, the support frame and the covering being shaped so as to define a downstream skirt;
a plurality of prosthetic leaflets, coupled to at least one element selected from the group consisting of: the support frame and the covering; and
a plurality of subvalvular anchoring elements, coupled to the downstream skirt, and configured to anchor the prosthetic valve to the native valve by piercing native leaflets of the native valve, passing through to a subvalvular space, and applying a force against the ventricular surface of the native leaflets.

For some applications, the prosthetic valve is configured to assume collapsed and expanded states.

For some applications, each of the tissue coupling elements is shaped as an element selected from the group consisting of: a hollow needle, a solid needle, a rod, and a rectangular plate.

For some applications, the tissue coupling elements are configured to assume a curved shape when in resting states.

For some applications, the tissue coupling elements are shaped so as to define respective barbs.

For some applications, the tissue coupling elements include needles.

For some applications, the needles are configured to assume curved shapes when in resting states.

For some applications, the needles are shaped so as to define respective lumens, and the apparatus further includes an implantation tool, which includes a plurality of rigid rods initially positioned in the lumens, respectively, so as to at least partially straighten the needles.

For some applications, the needles include a shape memory alloy.

There is additionally provided, in accordance with some applications of the present invention, apparatus including a prosthetic atrioventricular valve for coupling at a native valve, the prosthetic valve including:

a support frame;

a covering, which at least partially covers the support frame, the support frame and the covering being shaped so as to define an upstream annular skirt;

a plurality of prosthetic leaflets, coupled to at least one element selected from the group consisting of: the support frame and the covering;

a plurality of longitudinal members, coupled to the upstream annular skirt at respective sites; and a plurality of tissue anchors, configured to be guided along the longitudinal members, respectively, and to couple the upstream annular skirt to cardiac tissue in a vicinity of the native valve.

For some applications, the prosthetic valve is configured to assume collapsed and expanded states.

For some applications, the tissue anchors are configured to pass over the respective longitudinal members.

For some applications, the longitudinal members include respective wires, and the tissue anchors are configured to be guided along the respective wires.

For some applications, each of the tissue anchors includes a coupling element that is shaped so as to define a shape selected from the group consisting of: a helix, a spiral, a corkscrew, and a screw shaft.

For some applications, the longitudinal members are removably coupled to the upstream annular skirt at the respective sites.

For some applications, the prosthetic valve further includes a downstream skirt.

For some applications, the prosthetic valve further includes a ventricular anchoring assembly, which includes:

a ventricular tissue anchor; and a ventricular longitudinal member, a first end of which is coupled to the support structure, and a second end of which is coupled to the ventricular tissue anchor.

There is further provided, in accordance with some applications of the present invention, a method including:

providing a prosthetic atrioventricular valve, which includes (a) a support frame, (b) a covering, which at least partially covers the support frame, the support frame and the covering being shaped so as to define a downstream skirt, (c) a plurality of prosthetic leaflets, coupled to at least one element selected from the group consisting of: the support frame and the covering, and (d) an elongated anchoring member;

placing the prosthetic valve at a native valve of a subject, such that the downstream skirt passes through an orifice of the native valve toward a ventricle of the subject: and anchoring the prosthetic valve to the native valve by positioning the elongated anchoring member around the downstream skirt in a subvalvular space, such that the anchoring member presses native leaflets of the native valve against the downstream skirt.

For some applications, the prosthetic valve further includes a contracting housing shaped so as to define a channel therethrough, a first end of the anchoring member being fixed to the contracting housing, and a second end of the anchoring member passing through the channel, and anchoring further includes pulling on the second end of the anchoring member to tighten the anchoring member around the native leaflets.

For some applications, placing the prosthetic valve includes delivering the prosthetic valve to the native valve while the prosthetic valve is in a collapsed state in a catheter, and deploying the prosthetic valve from the catheter such that prosthetic valve assumes an expanded state.

There is further provided, in accordance with some applications of the present invention, a method including:

providing a prosthetic atrioventricular valve, which includes (a) a support frame, (b) a covering, which at least partially covers the support frame, the support frame and the covering being shaped so as to define a downstream skirt, (c) a plurality of prosthetic leaflets, coupled to at least one element selected from the group consisting of the support frame and the covering, and (d) a plurality of subvalvular anchoring elements, coupled to the downstream skirt;

placing the prosthetic valve at a native valve of a subject, such that the downstream skirt passes through an orifice of the native valve toward a ventricle of the subject; and anchoring the prosthetic valve to the native valve by causing the subvalvular anchoring elements to pierce native leaflets of the native valve, pass through to a subvalvular space, and apply a force against the ventricular surface of the native leaflets.

For some applications, placing the prosthetic valve includes delivering the prosthetic valve to the native valve while the prosthetic valve is in a collapsed state in a catheter, and deploying the prosthetic valve from the catheter such that the prosthetic valve assumes an expanded state.

For some applications, placing includes placing the prosthetic valve such that the downstream skirt pushes aside and presses against the native leaflets.

For some applications, the needles are shaped so as to define respective lumens, and anchoring includes causing the subvalvular anchoring elements to pierce the native leaflets while a rigid rods are initially positioned in the lumens, respectively, so as to at least partially straighten the needles, and subsequently withdrawing the rods from the lumens.

There is further provided, in accordance with some applications of the present invention, a method including:

providing a prosthetic atrioventricular valve, which includes (a) a support frame, (b) a covering, which at least partially covers the support frame, the support frame and the covering being shaped so as to define an upstream annular skirt, (c) a plurality of prosthetic leaflets, coupled to at least one element selected from the group consisting of: the support frame and the covering, and (d) a plurality of longitudinal members, coupled to the upstream annular skirt at respective sites;

placing the prosthetic valve at a native valve of a subject, such that the upstream annular skirt rests against a native annulus of the native valve, and the longitudinal members extend into an atrium of the subject;

guiding a plurality of tissue anchors along the longitudinal members respectively; and using the anchors, coupling the upstream annular skirt to cardiac tissue in a vicinity of the native valve.

For some applications, the method further includes decoupling the elongated members from the upstream annular skirt.

For some applications, the method further includes, after placing the prosthetic valve at the native valve and before coupling the upstream annular skirt to the cardiac tissue using the tissue anchors, temporarily anchoring the prosthetic valve to a ventricular wall of the subject using one or more ventricular cords.

For some applications, placing the prosthetic valve includes delivering the prosthetic valve to the native valve while the prosthetic valve is in a collapsed state in a catheter, and deploying the prosthetic valve from the catheter such that the prosthetic valve assumes an expanded state.

For some applications, placing the prosthetic valve includes placing the prosthetic valve at the native valve such that the longitudinal members pass through the catheter.

For some applications, the prosthetic valve further includes a downstream skirt, and placing includes placing the prosthetic valve at the native valve such the downstream skirt passes through an orifice of the native valve toward a ventricle of the subject.

For some applications, placing includes placing the prosthetic valve such that the downstream skirt pushes aside and presses against native leaflets of the native valve.

The present invention will be more fully understood from the following detailed description of applications thereof, taken together with the drawings, in which:

BRIEF DESCRIPTION OF THE DRAWINGS

FIGS. 8A-G are schematic illustrations of a valve contraction tool and a procedure for the use thereof, in accordance with an application of the present invention.

DETAILED DESCRIPTION OF APPLICATIONS

Figure 1:
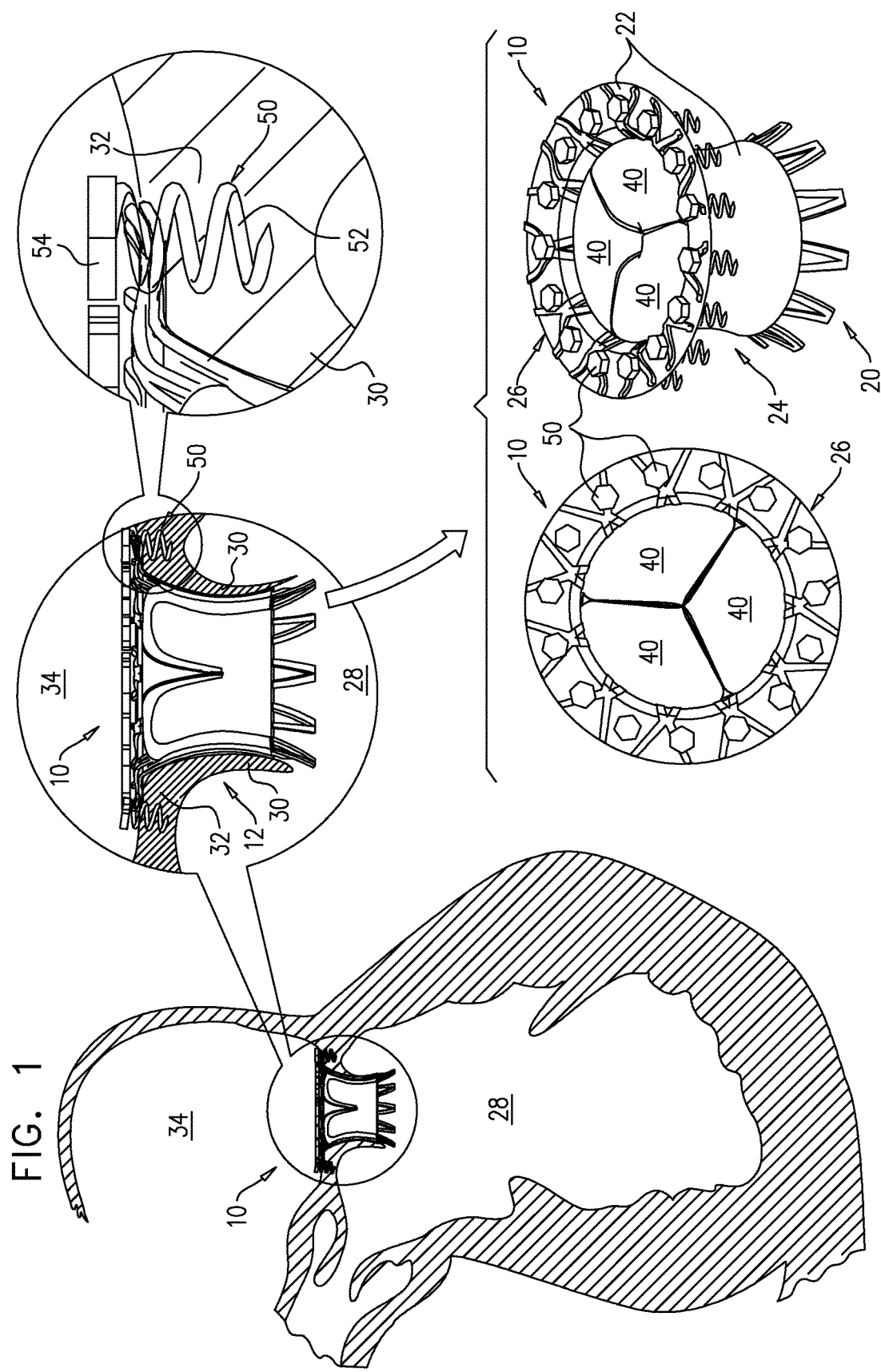
FIG. 1 is a schematic illustration of a collapsible prosthetic valve, in accordance with an application of the present invention.

FIG. 1 is a schematic illustration of a collapsible prosthetic valve 10, in accordance with an application of the present invention. Prosthetic valve 10 is configured for implantation in and/or at least partial replacement of a native atrioventricular valve 12 of a patient, such as a native mitral valve or a native tricuspid valve. The prosthetic valve is typically configured to assume a collapsed state for minimally-invasive delivery to the diseased native valve, such as by percutaneous or transluminal delivery using one or more catheters. FIG. 1 and the other figures show the prosthetic valve in an expanded state after delivery to the native valve.

Prosthetic valve 10 comprises a collapsible flexible support frame 20, which is at least partially covered by a covering 22. The prosthetic valve is shaped so as to define a downstream skirt 24 and an upstream annular skirt 26. The downstream skirt is configured to be placed at native valve 12, such that the downstream skirt passes through the orifice of the native valve and extends towards, and, typically partially into, a ventricle 28. The downstream skirt typically pushes aside and presses against native leaflets 30 of native valve 12, which are typically left in place during and after implantation of the prosthetic valve. The upstream annular skirt is configured to be placed around a native annulus 32 of the native valve, and to extend at least partially into an atrium 34 such that annular skirt rests against the native annulus. The annular skirt is typically too large to pass through the annulus, and may, for example, have an outer diameter of between 30 and 60 mm.

For some applications, collapsible support frame 20 comprises a stent, which comprises a plurality of struts. The struts may comprise, for example, a metal such as Nitinol or stainless steel. For some applications, covering 22 comprises a fabric, such as a woven fabric, e.g., Dacron. Covering 22 is typically configured to cover at least a portion of downstream skirt 24, and at least a portion of upstream annular skirt 26, such as the entire annular skirt (as shown in FIG. 1). The covering may comprise a single piece, or a plurality of pieces sewn together.

Prosthetic valve 10 further comprises a plurality of valve leaflets 40, which may be artificial or tissue-based. The leaflets are typically coupled to an inner surface of the valve prosthesis, such as near the junction between the downstream and upstream skirts 24 and 26. The leaflets are coupled, e.g., sewn, to frame 20 and/or covering 22. For applications in which the prosthetic valve is configured to be implanted at the native mitral valve, the prosthetic valve typically comprises three leaflets 40, such as shown in FIG. 1.

For some applications, such as shown in FIG. 1, prosthetic valve 10 comprises a plurality of tissue anchors 50 for coupling the prosthetic valve to native valve 12, such as the mitral valve. The anchors are typically distributed approximately evenly around upstream annular skirt 26, and couple the upstream skirt to native annulus 32. Typically, each of anchors 50 comprises a tissue-coupling element 52 coupled to a base 54. Tissue-coupling element 52 is configured to pass through upstream annular skirt 26 and penetrate the tissue of the native annulus, and may, for example, be shaped as a corkscrew, spiral, helix, or screw shaft. Base 54 is configured to be too large to pass through the upstream annular skirt. The tissue-coupling element is advanced into the tissue, such as by rotation, until the base comes in contact with and is held tightly against the upstream side of the upstream annular skirt, thus creating a seal between the upstream skirt and the native annulus. For some applications, prosthetic valve 10 comprises between 5 and 20 anchors, such as between 10 and 15 anchors, e.g., 15 anchors. It is noted that, unlike in some prior techniques for coupling prosthetic valves to native valve sites, sutures are typically not used for coupling prosthetic valve 10 to the native valve site.

Figure 2A:
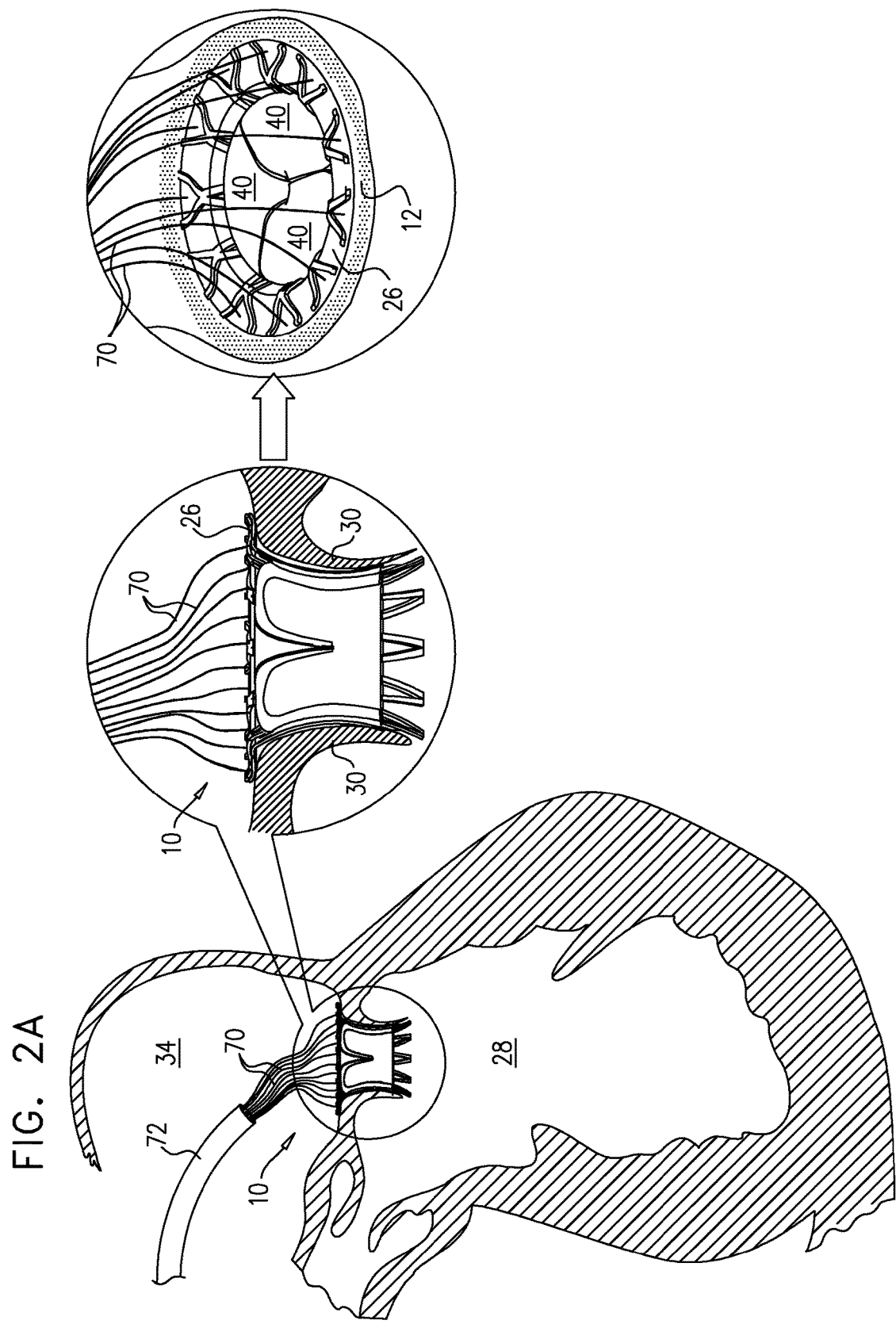
FIGS. 2A-B are schematic illustrations of a technique for anchoring the prosthetic valve of FIG. 1 at a native valve, in accordance with an application of the present invention.
Figure 2B:
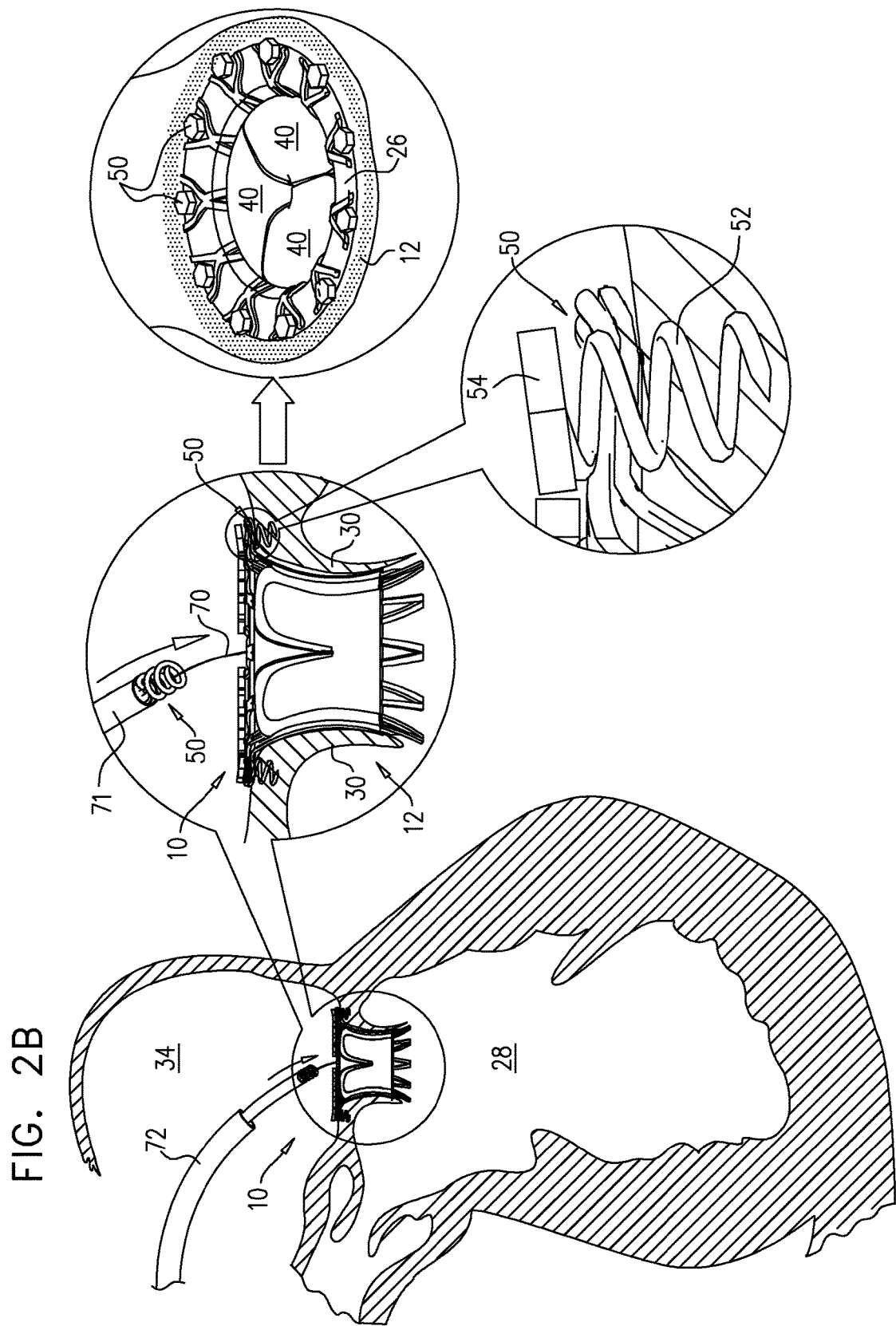

Reference is now made to FIGS. 2A-B, which are schematic illustrations of a technique for anchoring prosthetic valve 10 at native valve 12, in accordance with an application of the present invention. In this application, prosthetic valve 10 is at least initially coupled to a plurality of flexible elongated members 70, such as wires, cords, or sutures. Elongated members 70 are typically removably coupled to upstream annular skirt 26 at respective sites at which respective tissue anchors 50 subsequently pass through the skirt.

As shown in FIG. 2A, during an implantation procedure, the surgeon places prosthetic valve 10 at a desired location at native valve 12. Elongated members 70 extend into atrium 34, and typically pass through a catheter 72 used to perform the implantation procedure, optionally the same catheter through which prosthetic valve 10 is deployed into the atrium. Optionally, the prosthetic valve is temporarily held in place using the anchoring techniques described hereinbelow with reference to FIGS. 4A-C (or permanently held in place using such anchoring, in combination with the anchoring described hereinbelow with reference to FIG. 2B). For example, the prosthetic valve may be temporarily anchored to the ventricular wall, such as to the apex or one or more papillary muscles, using one or more ventricular cords, as described hereinbelow.

Subsequently, as shown in FIG. 2B, each of anchors 50 is guided along (e.g., passed over, or alongside) a respective one of elongated members 70, until the anchor reaches upstream annular skirt 26. The anchor is coupled to cardiac tissue, such as by using a rotation tool 71 that is separately passed over each of elongated members 70. Typically, the elongated member is then decoupled from upstream annular skirt 26. For example, a cutting tool may be used to decouple the elongated member from the skirt; the cutting tool may be passed through catheter 72, and/or guided along the elongated member. Alternatively, the elongated member may be looped through the skirt, such that both ends of the elongated member remain outside of the patient's body. The surgeon decouples the elongated member from the skirt by releasing one end of the elongated member and pulling on the other end, until the elongated member is drawn from the skirt. Alternatively, the elongated member is cut at some distance from upstream annular skirt 26, such that a portion of the elongated member remains coupled to the upstream annular skirt. These steps are repeated for each of the anchors and elongated members.

These techniques enable the surgeon to readily bring the anchors to the appropriate sites of the upstream annular skirt, without the need for excessive imaging, such as fluoroscopy.

Figure 3A:
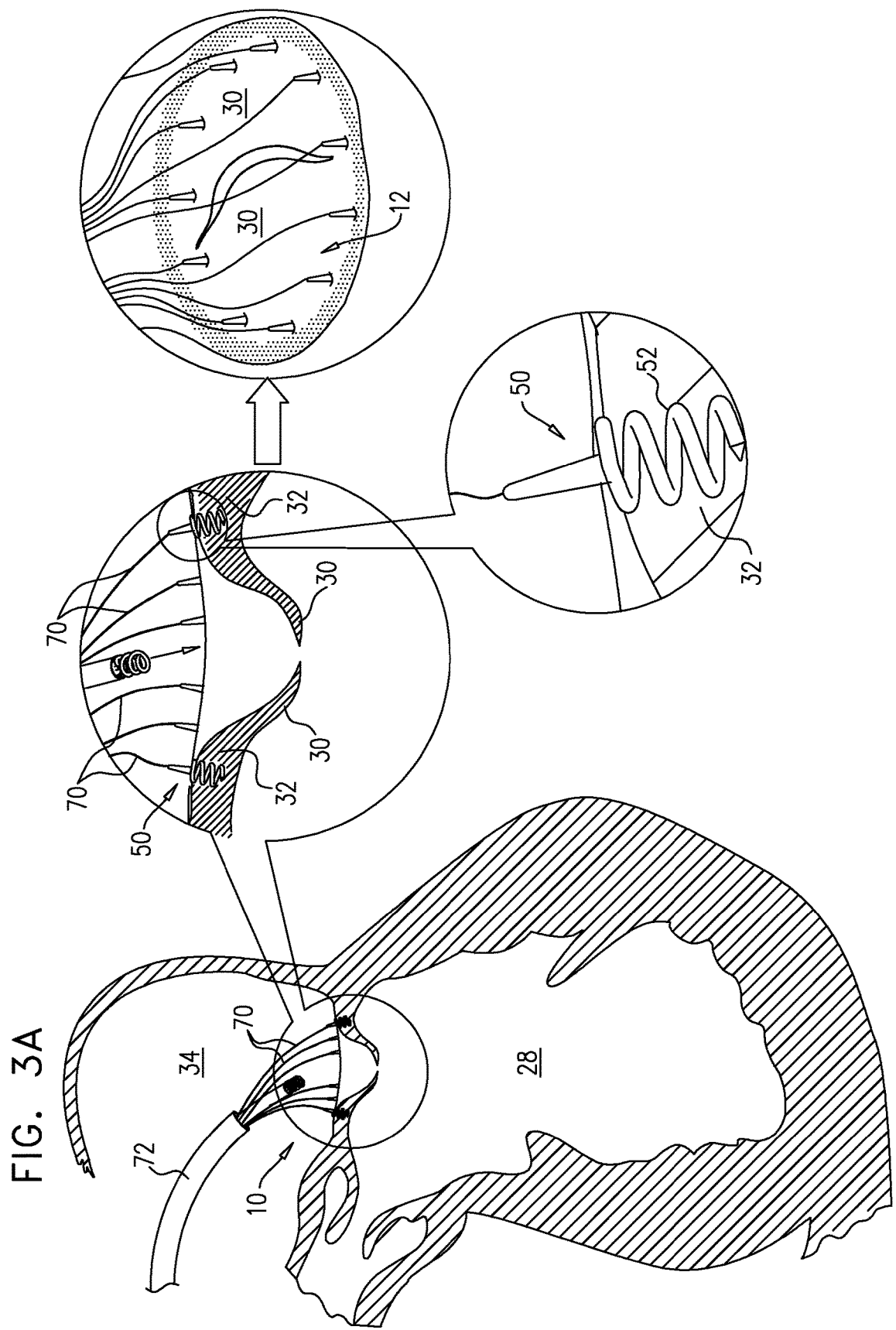
FIGS. 3A-B are schematic illustrations of another technique for anchoring the prosthetic valve of FIG. 1 at the native valve, in accordance with an application of the present invention.
Figure 3B:
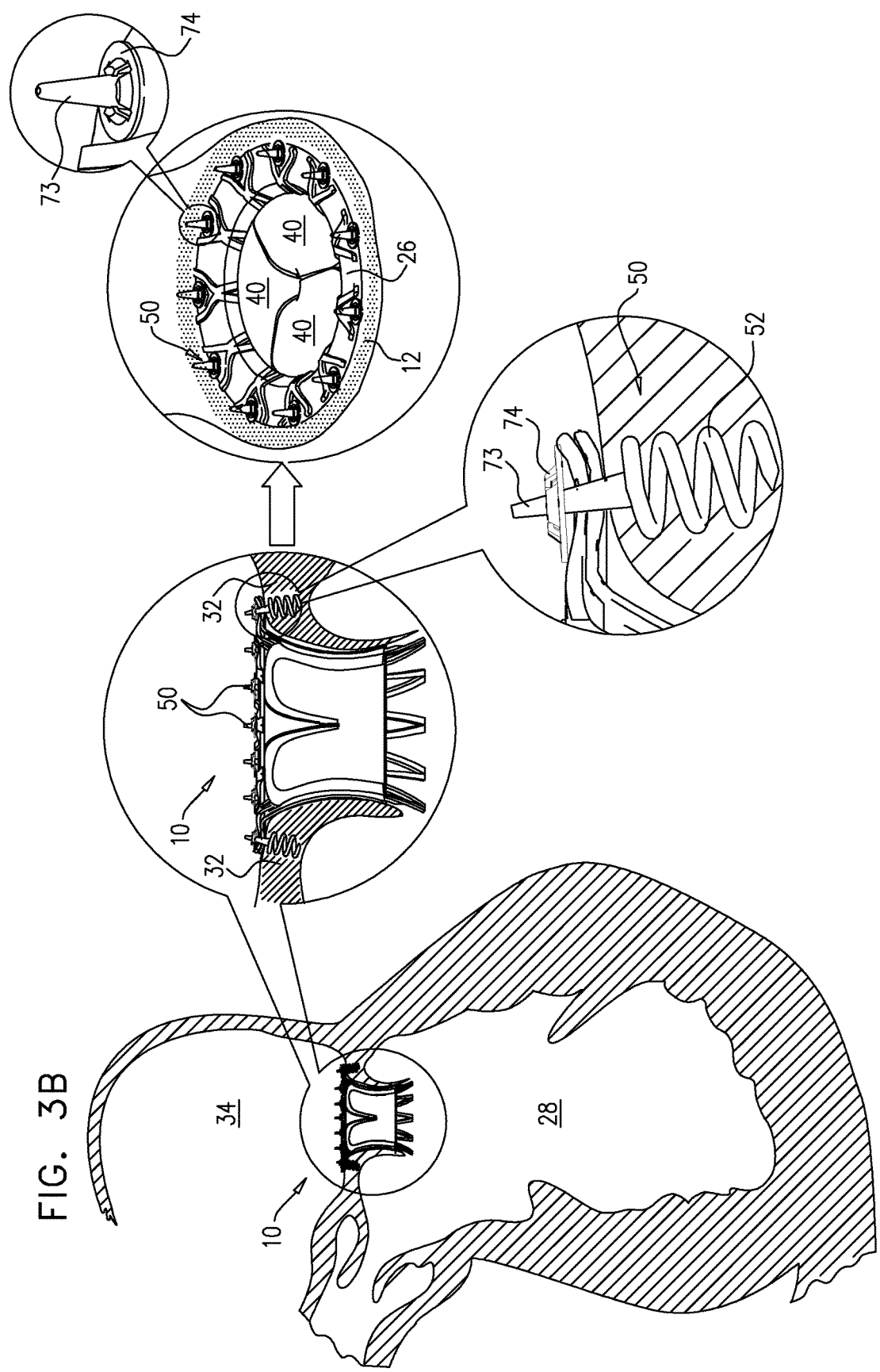

Reference is made to FIGS. 3A-B, which are schematic illustrations of another technique for anchoring prosthetic valve 10 at native valve 12, in accordance with an application of the present invention. In this application, anchors 50 are initially coupled to respective flexible elongated members 70, such as wires, cords, or sutures. For some applications, each of the anchors comprises an upstream post 73, to which a respective elongated member 70 is coupled. Optionally, the posts comprise a flexible material, such as silicone.

As shown in FIG. 3A, during an implantation procedure, the surgeon couples anchors 70 to respective sites of cardiac tissue on native annulus 32. For example, the surgeon may use a rotation tool passed along (e.g., over or alongside) each of elongated members 70.

Subsequently, as shown in FIG. 3B, the surgeon passes prosthetic valve 10 over elongated members 70, until the prosthetic valve reaches the native valve and upstream annular skirt 26 rests against the atrial side of native annulus 32. In order to guide the prosthetic valve to the anchors and desired anatomical position, elongated members 70 pass through respective locations on upstream annular skirt 26. Upstream annular skirt 26 is then coupled to the anchors, e.g., posts 73 thereof, to hold the prosthetic valve in place at the native annulus, creating a seal between the upstream skirt and the native annulus. This anchoring technique typically reshapes the native annulus to assume a rounder shape, similar to that of the prosthetic valve.

For some applications, respective coupling, elements 74 are used to couple the skirt to the posts of the anchors. The coupling elements may be passed over elongated members 70. For example, the coupling elements may be shaped as discs with inwardly-facing teeth that engage the posts, and prevent removal of the disc from the posts. The elongated members are subsequently decoupled from anchors 50. For example, a cutting tool may be used to decouple the elongated members from the anchors; the cutting tool may be passed through catheter 72, and/or guided along the elongated member. Alternatively, the elongated members may be looped through the anchors, such that both ends of each elongated member remain outside of the patient's body. The surgeon decouples the elongated member from the anchor by releasing one end of the elongated member and pulling on the other end, until the elongated member is drawn from the anchor.

Figure 4A:
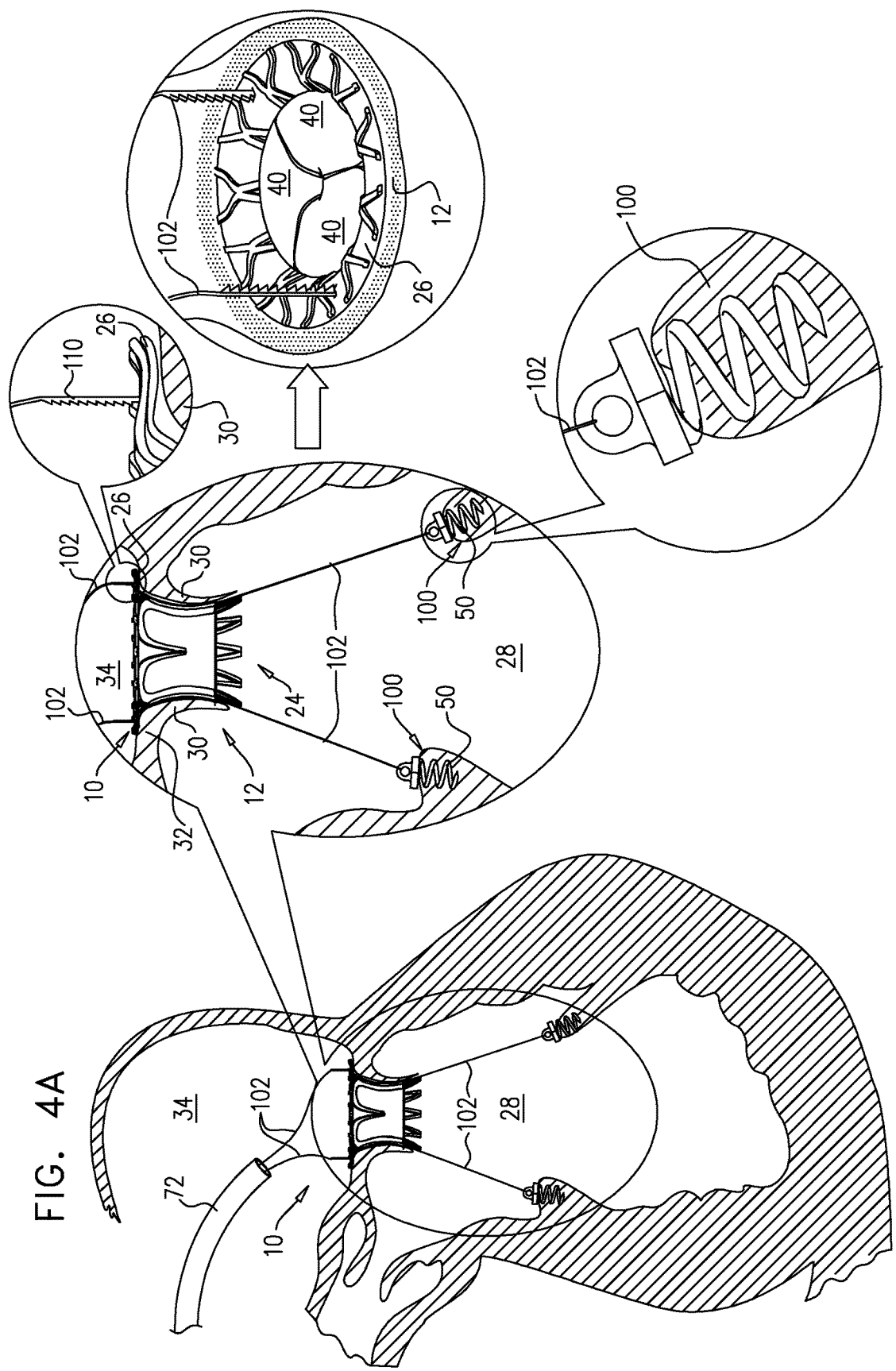
FIGS. 4A-C are schematic illustrations of yet another technique for anchoring the prosthetic valve of FIG. 1 at the native valve, in accordance with respective applications of the present invention.
Figure 4B:
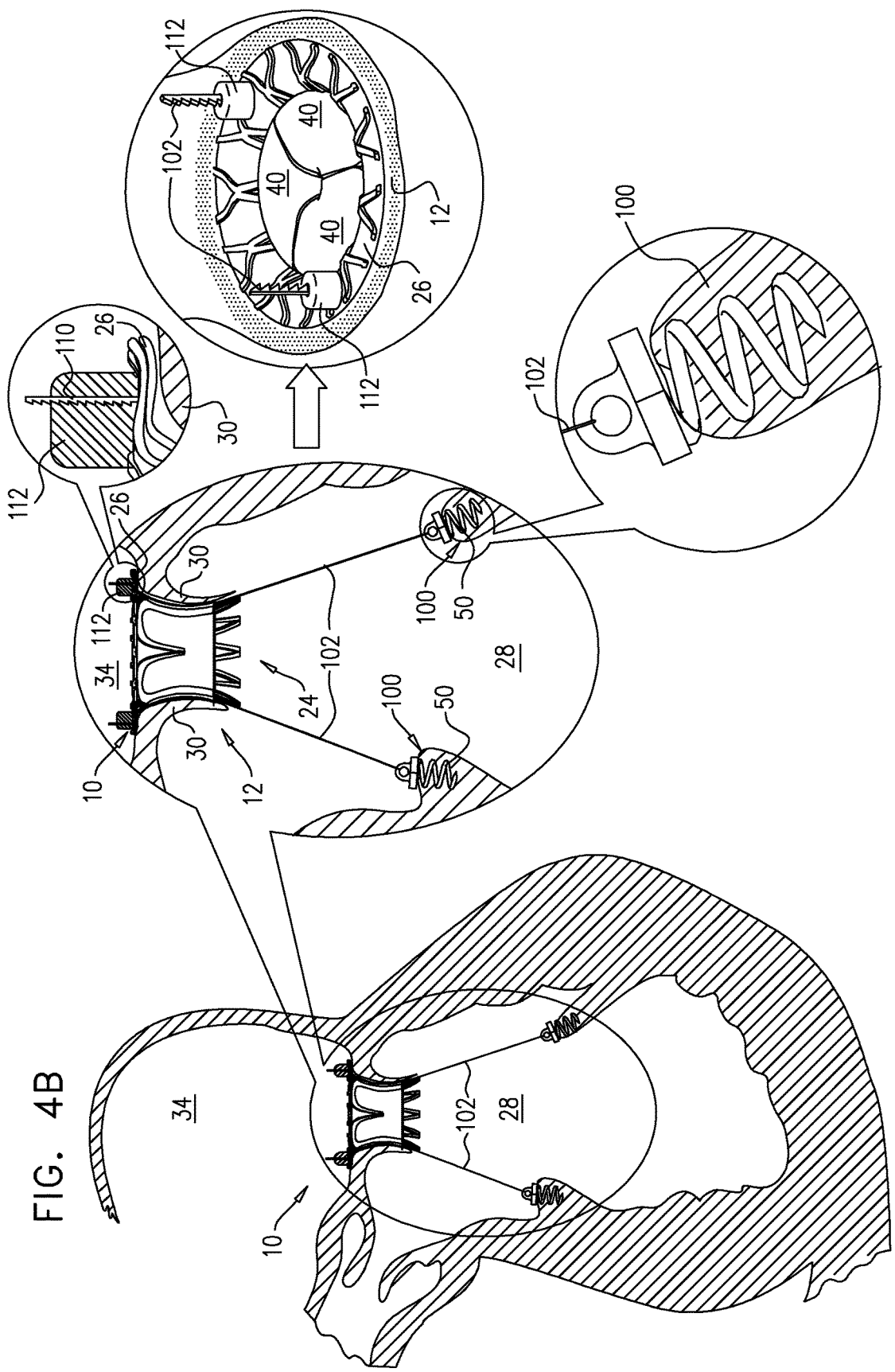
Figure 4C:
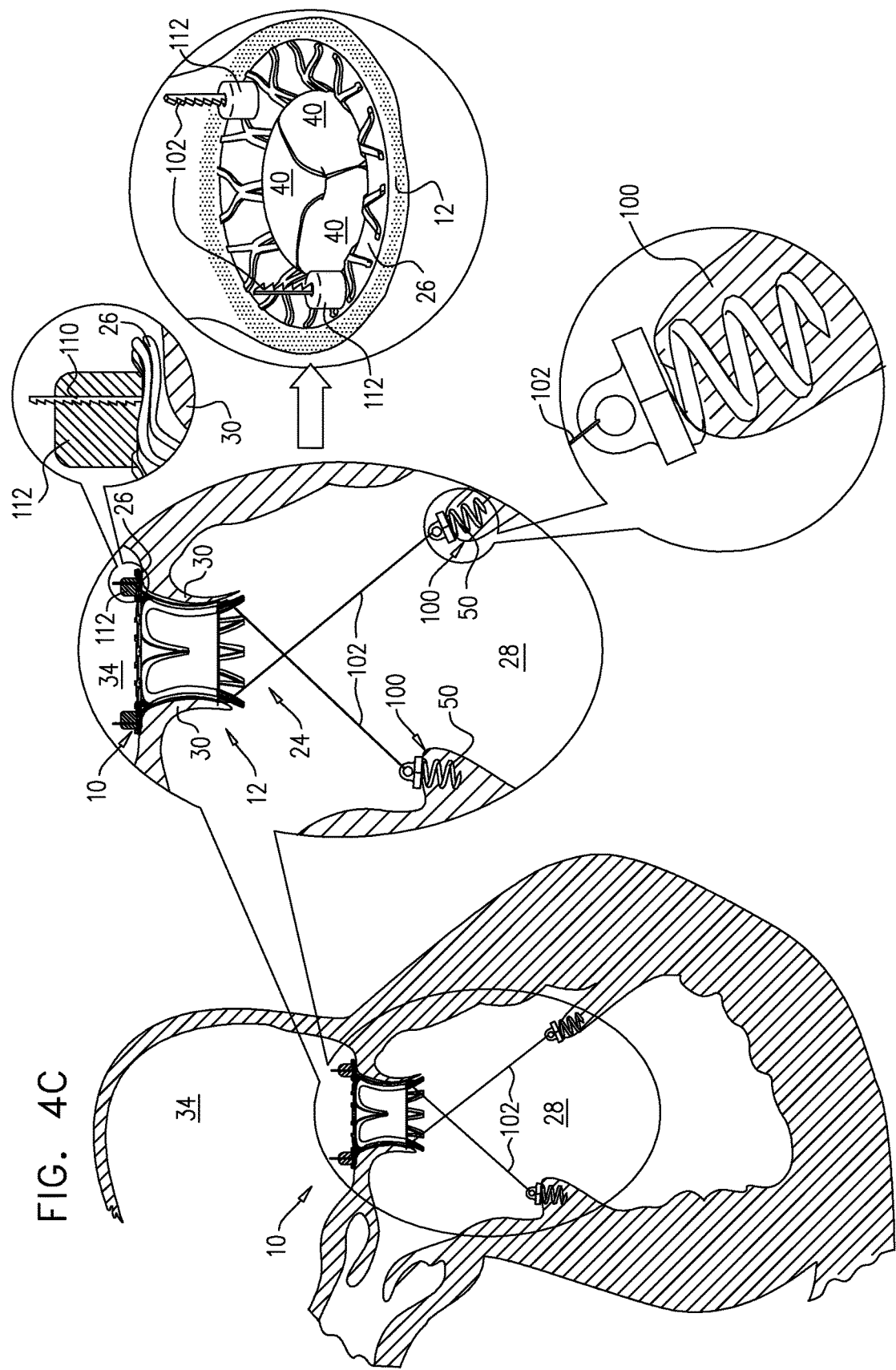

Reference is made to FIGS. 4A-C, which are schematic illustrations of another technique for anchoring prosthetic valve 10 at native valve 12, in accordance with respective applications of the present invention. In these applications, prosthetic valve 10 is held in place at native valve 12 by a ventricular anchoring assembly. The ventricular anchoring assembly comprises one or more ventricular longitudinal members, such as ventricular cords 102, and one or more respective ventricular tissue anchors 50, described hereinabove. The ventricular cords are coupled, using the respective anchors, to respective ventricular sites, such as respective papillary muscles 100 (as shown in FIGS. 4A-C) or other locations of the ventricular wall, such as near the apex of ventricle 28 (configuration not shown). The cords pull prosthetic valve 10 toward ventricle 28, such that upstream annular skirt 26 is pulled tightly against native annulus 32. As mentioned above, the upstream annular skirt is too large to pass through the native annulus, and is thus held in place by the cords.

For some applications, in order to tense ventricular cords 102, prosthetic valve 10 and upstream portions 110 of the cords are configured to provide one-way upstream motion of the cords with respect to the prosthetic valve, and to prevent distal motion of the cords. For example, upstream portions 110 of the cords may be shaped so as to define a one-way ratchet, which can pass through upstream annular skirt 26 in an upstream direction, but not in a downstream direction. After the cords have been anchored to the ventricular sites and the prosthetic valve has been placed in position at the native annulus, the surgeon pulls upstream on the upstream ends of the cords, in order to tense the cords. Optionally, as shown in FIGS. 4B and 4C, upstream annular skirt 26 comprises ratcheting elements 112, through which ratcheted upstream portions 110 of ventricular cords 102 pass, in order to prevent such downstream motion.

For some applications, in order to provide access to anchors 50 during coupling of the anchors to the ventricular sites, the surgeon first introduces the anchors and cords into the ventricle, thereafter couples the anchors to the ventricular sites, and subsequently positions the prosthetic valve at the native annulus. The cords may pass between downstream skirt 24 and native leaflets 30 (as shown in FIGS. 4A-C), or through the downstream skirt (configuration not shown).

For some applications, as shown in FIG. 4C, the surgeon crosses cords 102 in the ventricle, such that the cords assume an X-shape when viewed from the side. Such crossing may provide firmer anchoring of the prosthetic valve to the native annulus.

For some applications, the coupling techniques described with reference to FIGS. 4A-C effect ventricular remodeling, in addition to or instead of anchoring the prosthetic valve to the native valve site.

For some applications, instead of being coupled to upstream annular skirt 26 (as shown in FIGS. 4A-C), cords 102 are alternatively or additionally coupled to downstream skirt 24, such as to struts of the support frame thereof, e.g., at or near a downstream end of the downstream skirt (configuration not shown).

Figure 5A:
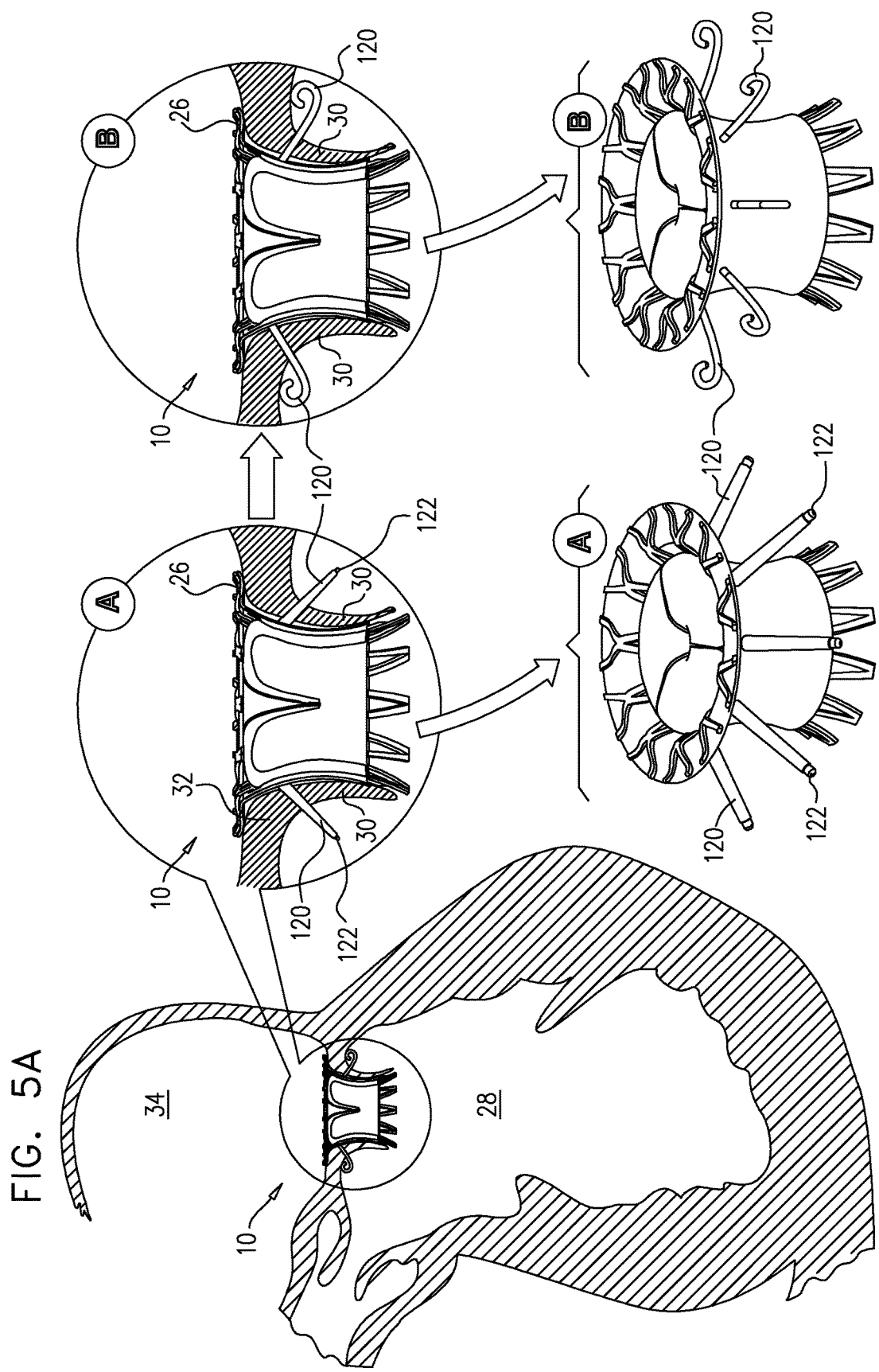
FIGS. 5A-C are schematic illustrations of additional techniques for anchoring the prosthetic valve of FIG. 1 at the native valve, in accordance with respective applications of the present invention.
Figure 5B:
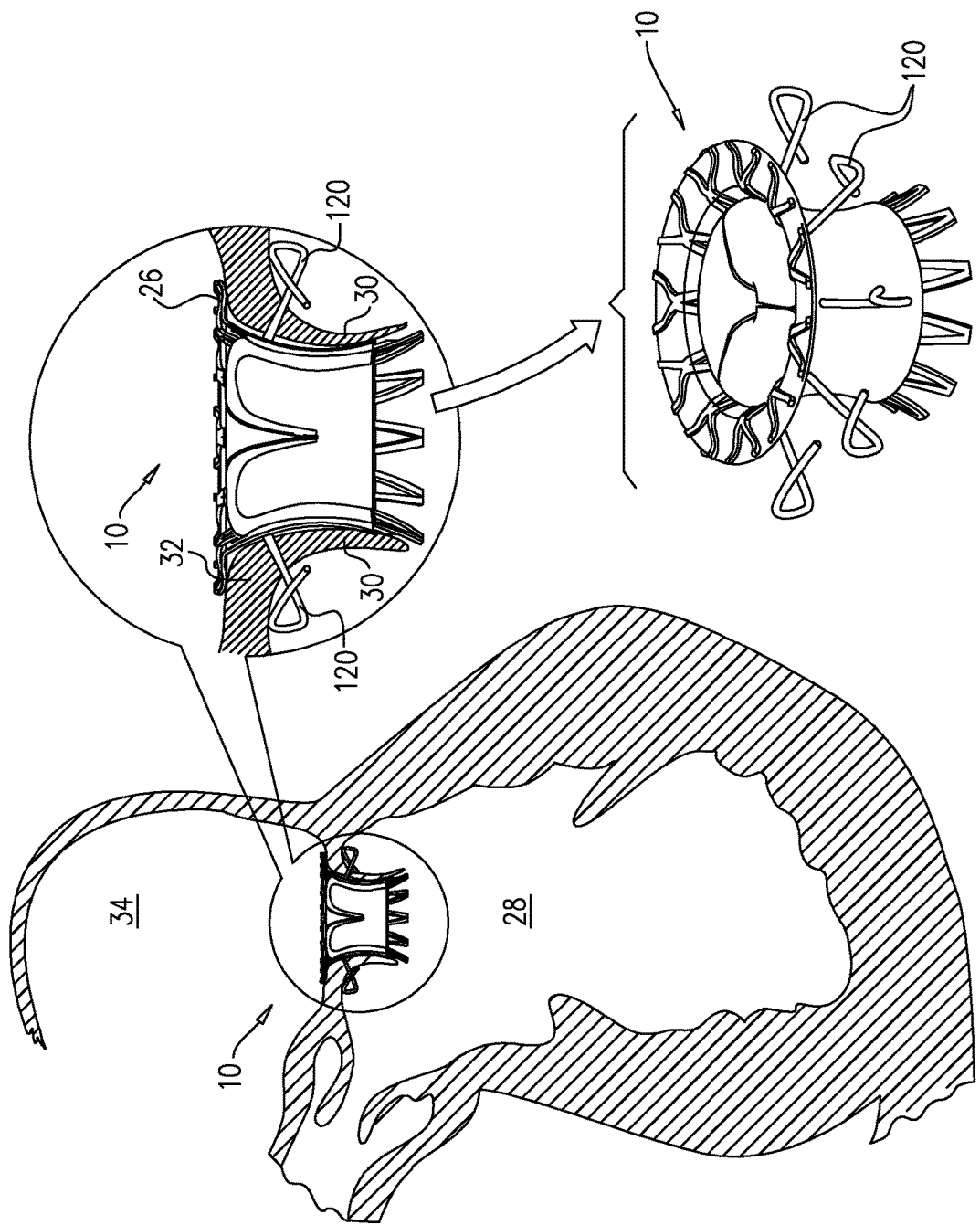
Figure 5C:
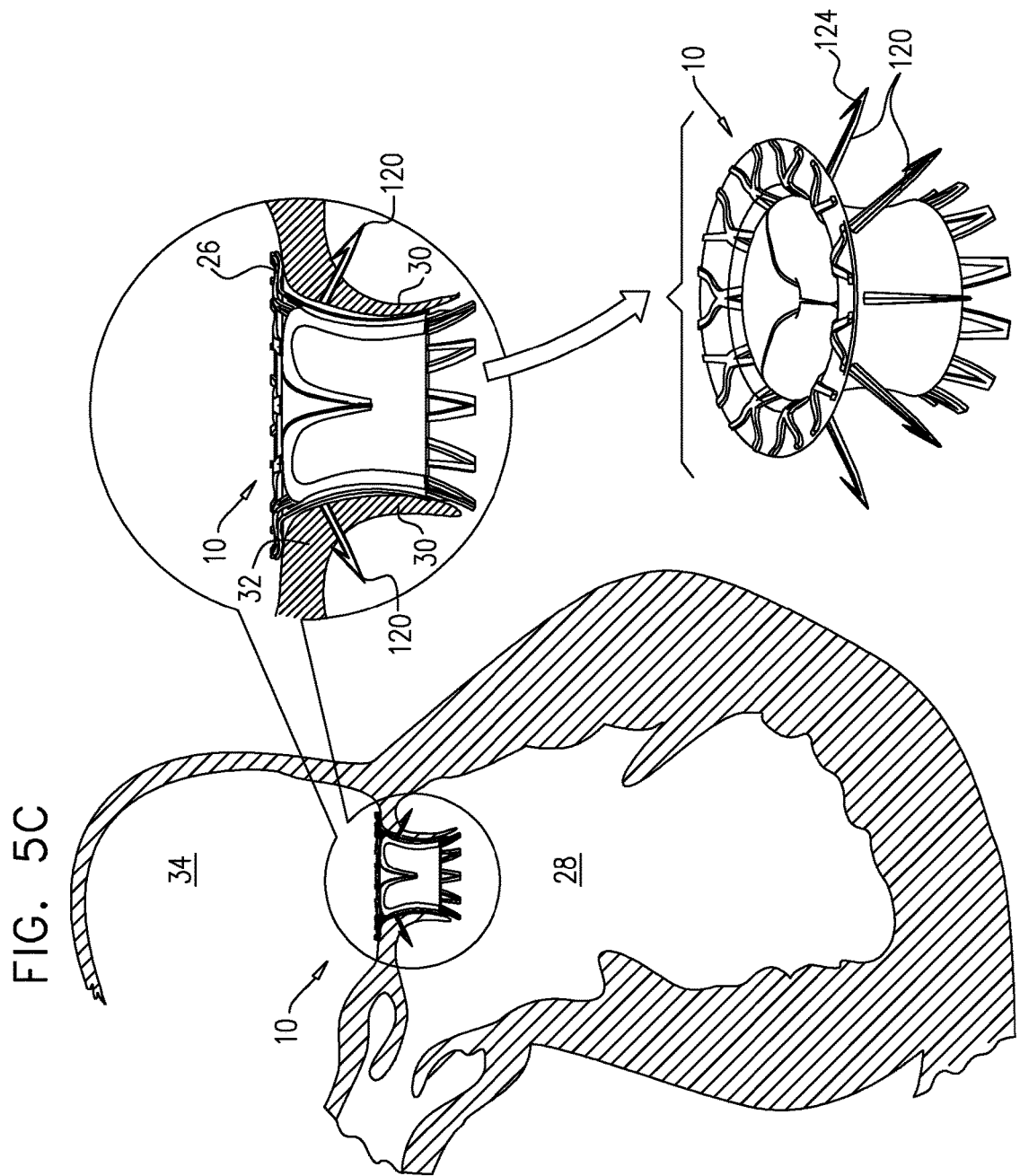

Reference is made to FIGS. 5A-C, which are schematic illustrations of additional techniques for anchoring prosthetic valve 10 at native valve 12, in accordance with respective applications of the present invention. In these applications, prosthetic valve 10 comprises one or more subvalvular anchoring elements 120, which are configured to pierce native leaflets 30 and pass through to a subvalvular space. Anchoring elements 120 are typically shaped and positioned to apply a force against the ventricular surface of native leaflets 30, thereby holding upstream annular skirt 26 against the native annulus. The anchoring elements are generally elongated (e.g., have a length of between 2 and 7 mm), and may, for example, be shaped as hollow needles, solid needles, rods, or rectangular plates. The anchoring elements typically comprise a metal, such as Nitinol.

For some applications, as shown in FIG. 5A, distal ends of anchoring elements 120 are curved toward upstream annular skirt 26, and thus toward the ventricular surface of the native annulus when the prosthetic valve is implanted. For other applications, as shown in FIG. 5B, the distal ends of the anchoring elements are folded. Alternatively or additionally (i.e., optionally in combination with the application shown in FIG. 5A or the application shown in FIG. 5B), the distal ends of the anchoring elements are shaped so as to define respective barbs 124, as shown in FIG. 5C.

For some applications, as shown in FIG. 5A, the anchoring elements are configured to assume a curved shape when in resting states. In order to more readily pierce the native leaflets, the anchoring elements are configured to initially assume a straighter shape during the implantation procedure. For example, as shown as configuration "A" of FIG. 5A, rigid rods 122 may be initially inserted into the lumens of the anchoring elements, which are shaped as hollow needles, in order to at least partially straighten the anchoring elements. After the anchoring elements have penetrated the native leaflets, rods 122 are withdrawn from the anchoring elements, and the anchoring elements assume their curved shapes, as shown as configuration "B" of FIG. 5A. For some applications, an implantation tool is provided that comprises rods 122. This technique may additionally be used in combination with the application shown in FIG. 5B or the application shown in FIG. 5C. Alternatively or additionally, the anchoring elements comprises a shape memory alloy that is configured to initially assume a straighter shape, e.g., at a first temperature, and subsequently a curved shape, e.g., at a second temperature.

Figure 6:
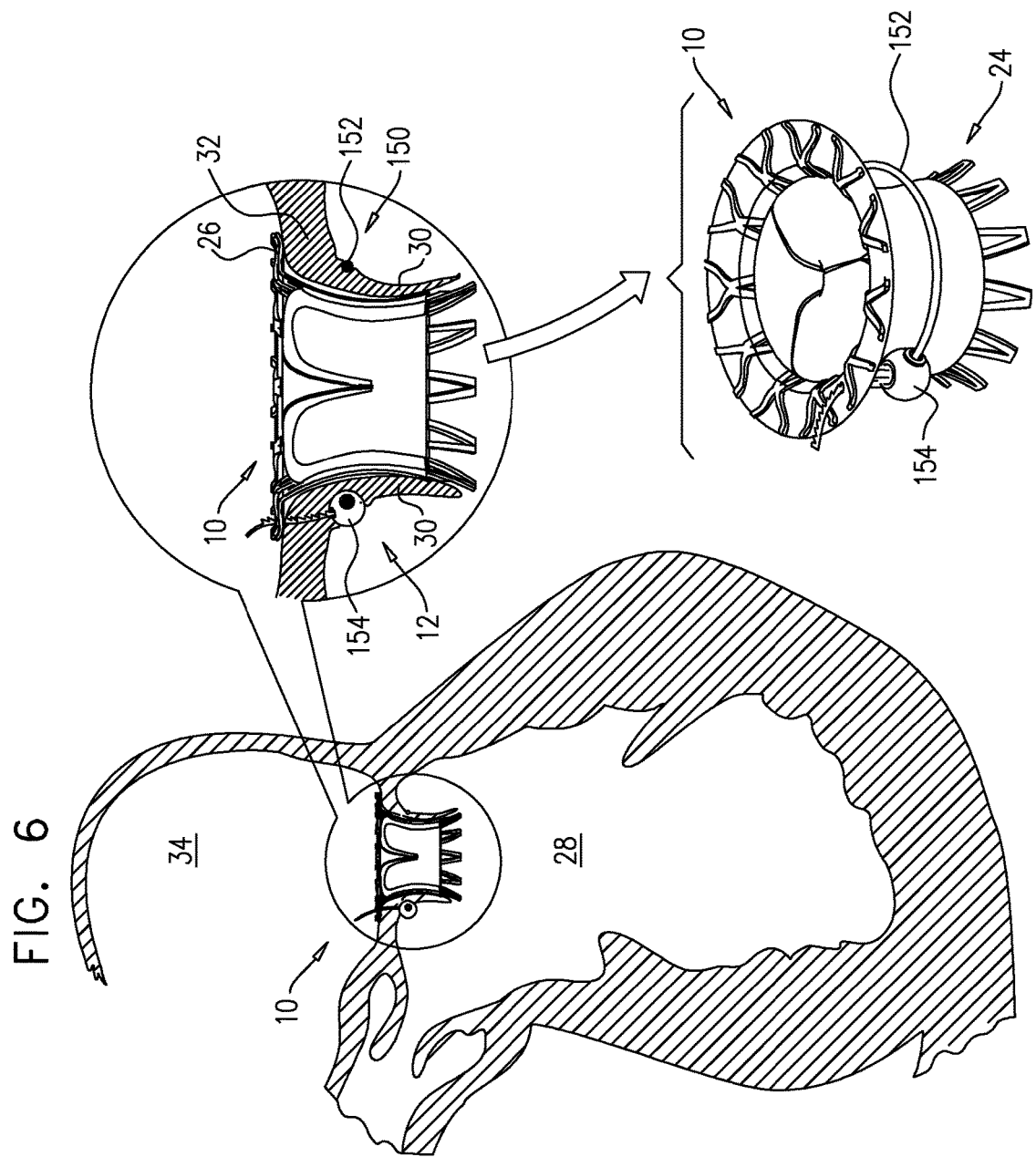
FIG. 6 is a schematic illustration of yet another technique for anchoring the prosthetic valve of FIG. 1 at the native valve, in accordance with an application of the present invention.

Reference is made to FIG. 6, which is a schematic illustration of yet another technique for anchoring prosthetic valve 10 at native valve 12, in accordance with an application of the present invention. In this application, prosthetic valve 10 comprises an elongated anchoring member 152, such as a cord, strip, wire, or suture. Anchoring member 152 is configured to be positioned around at least a radial portion of downstream skirt 24 and be positioned in a subvalvular space 150. When tightened, the anchoring member squeezes native leaflets 30 against downstream skirt 24, thereby fixing prosthetic valve 10 in place at the native valve, and creating a seal between the valve prosthesis and the native leaflets. For some applications, anchoring member 152 is positioned completely around, i.e., surrounds, downstream skirt 24. For some applications, the anchoring member is introduced into the subvalvular space and brought around the native leaflets using a guidewire that is introduced around the leaflets tangential to native annulus 32.

For some applications, valve prosthesis 10 further comprises a contracting housing 154. Typically, a first end of anchoring member 152 is fixed to the contracting housing, and a second end of the anchoring member passes through a channel of the contracting housing. Pulling on the second end of the anchoring member tightens the anchoring member around the native leaflets. For some applications, an upstream portion of the anchoring member is shaped so as to define a ratchet, which allows tightening, but not loosening, of the anchoring member.

Figure 7:
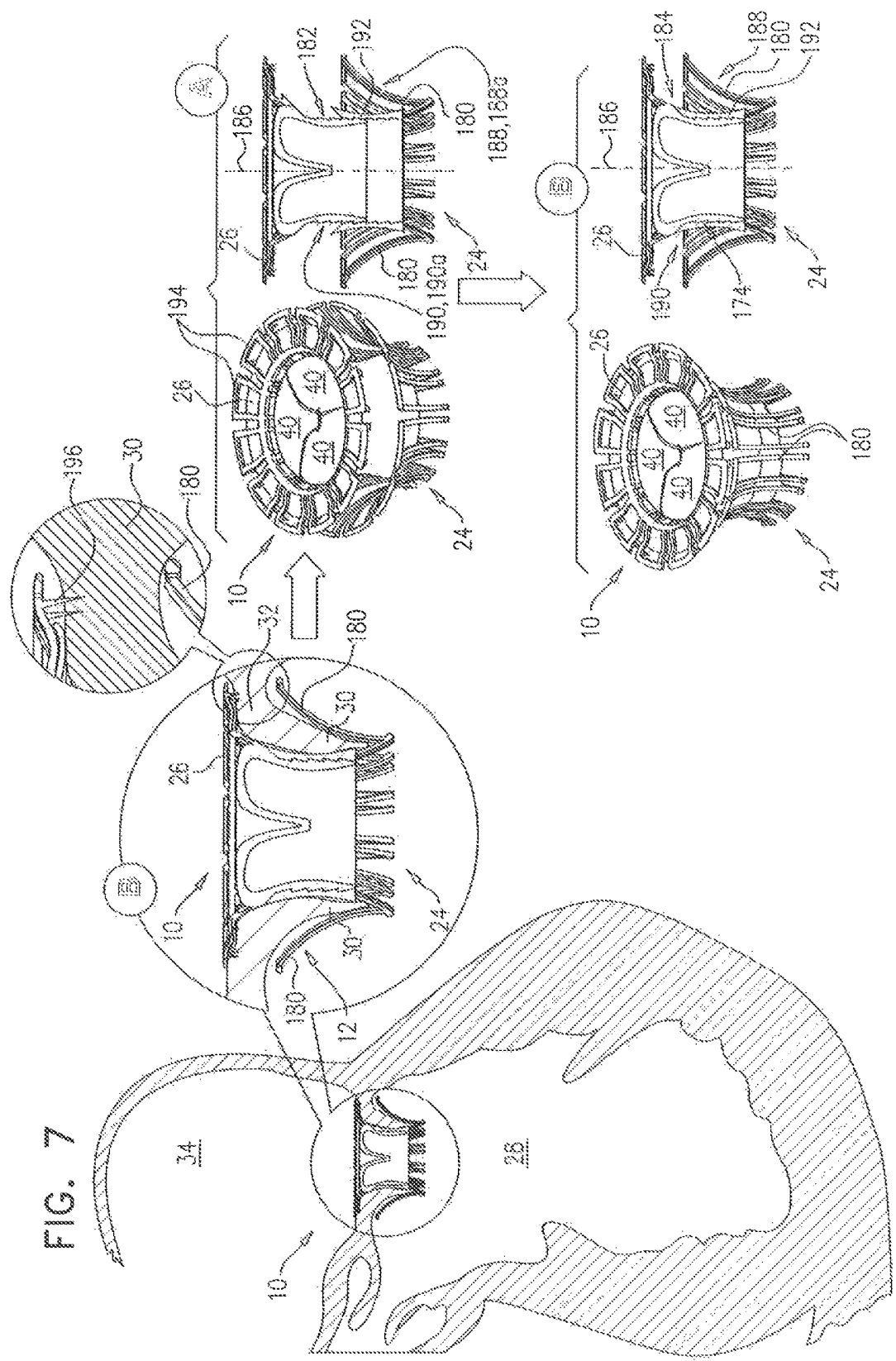
FIG. 7 is a schematic illustration of still another technique for anchoring the prosthetic valve of FIG. 1 at the native valve, in accordance with an application of the present invention.

Reference is made to FIG. 7, which is a schematic illustration of still another technique for anchoring prosthetic valve 10 at native valve 12, in accordance with an application of the present invention. In this application, downstream skirt 24 is shaped so as to define a plurality of anchoring arms 180, which extend in an upstream direction from a downstream end of downstream skirt 24 (as shown in FIG. 7), or from locations near the downstream end of the downstream skirt (configuration not shown). The coupling arms are configured to be positioned in the subvalvular space.

Prosthetic valve 10 is configured to assume two states: (a) an extended, unlocked state 182, shown as configuration "A" of FIG. 7, and (b) a contracted, locked state 184, shown as configuration "B" of FIG. 7. A longitudinal length of prosthetic valve 10 along a central longitudinal axis 186 thereof is greater when the prosthetic valve is in extended, unlocked state 182, than when the prosthetic valve is in contracted, locked state 184. The prosthetic valve is typically configured to allow one-way passage from unlocked state 182 to locked state 184. For example, mating downstream and upstream portions 188 and 190 of downstream skirt 24 may be shaped so as to define corresponding ratchet teeth 192, which allow downstream portion 188 to move in an upstream direction with respect to upstream portion 190, but not in a downstream direction with respect thereto. (In this regard, upstream portion 190 is a first portion of the downstream skirt, and downstream portion 188 is a second portion of the downstream skirt.)

During an implantation procedure, prosthetic valve 10 initially assumes extended, unlocked state 182. The prosthetic valve is advanced to native valve 12 in this unlocked state, and anchoring arms 180 are positioned such that native leaflets 30 are between the anchoring arms and the body of downstream skirt 24. The surgeon causes the prosthetic valve to assume contracted, locked state 184. In locked state 184 the anchoring arms squeeze and grasp native leaflets 30 and a portion of native annulus 32 between the anchoring arms, the body of the downstream skirt 24, and upstream annular skirt 26. In this application, upstream annular skirt 26 may comprise relative short upstream arms 194, which may correspond to and be aligned with anchoring arms 180 of downstream skirt 24. Optionally, upstream arms 194 may comprise one or more spikes 196, which are configured to pierce native annulus 32 in order to aid with anchoring.

FIGS. 8A-G are schematic illustrations of a valve contraction tool 200 and a procedure for the use thereof, in accordance with an application of the present invention. Valve contraction tool 200 is optionally used with the configuration of prosthetic valve 10 described hereinabove with reference to FIG. 7, in order to cause prosthetic valve 10 to transition from extended, unlocked state 182 to contracted, locked state 184.

As best seen in FIG. 8E, tool 200 comprises a catheter 220, and an upstream pushing tube (not shown), a downstream end of which is coupled to an upstream pushing adaptor 212. Upstream pushing adaptor 212 is configured to assume an umbrella-like shape when expanded, forming a downstream ring that is sized to rest and push against upstream annular skirt 26. Tool 200 further comprises a downstream pulling adaptor 214, which is coupled to a pulling wire 216. Downstream pulling adaptor 214 is configured to rest against the downstream end of downstream skirt 24. Pulling wire 216 is coupled to the downstream pulling adaptor (e.g., at a center thereof), and passes through upstream pushing adaptor 212 and the upstream pushing tube.

Figure 8A:
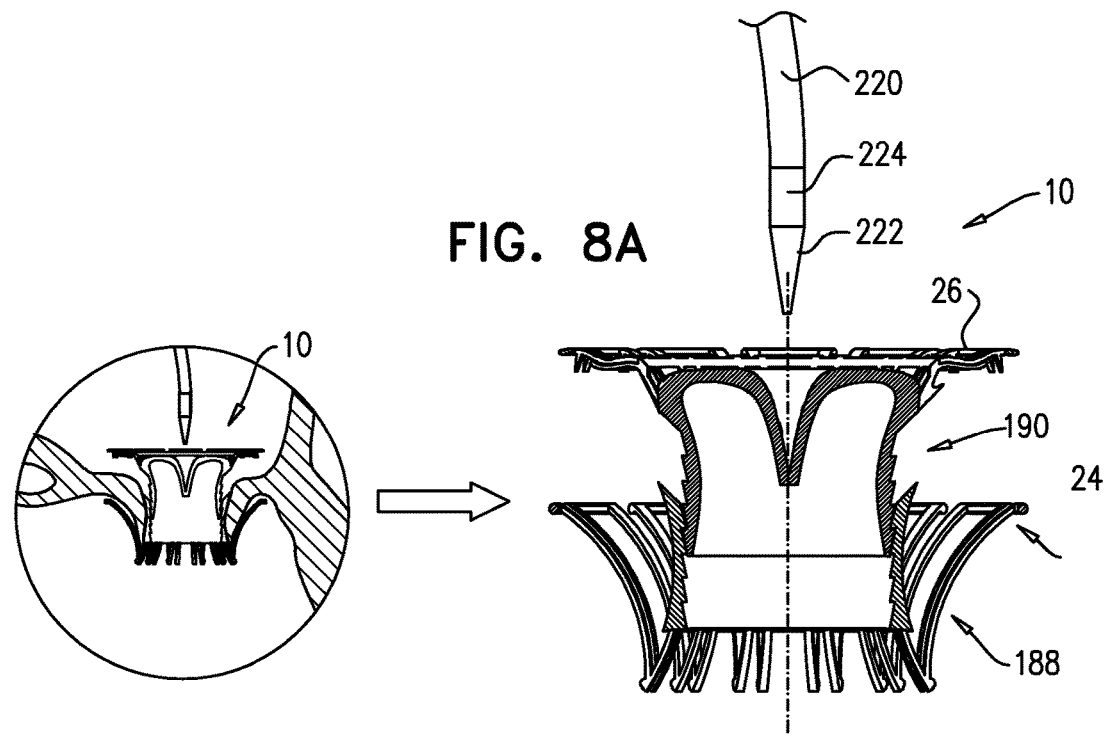
Figure 8B:
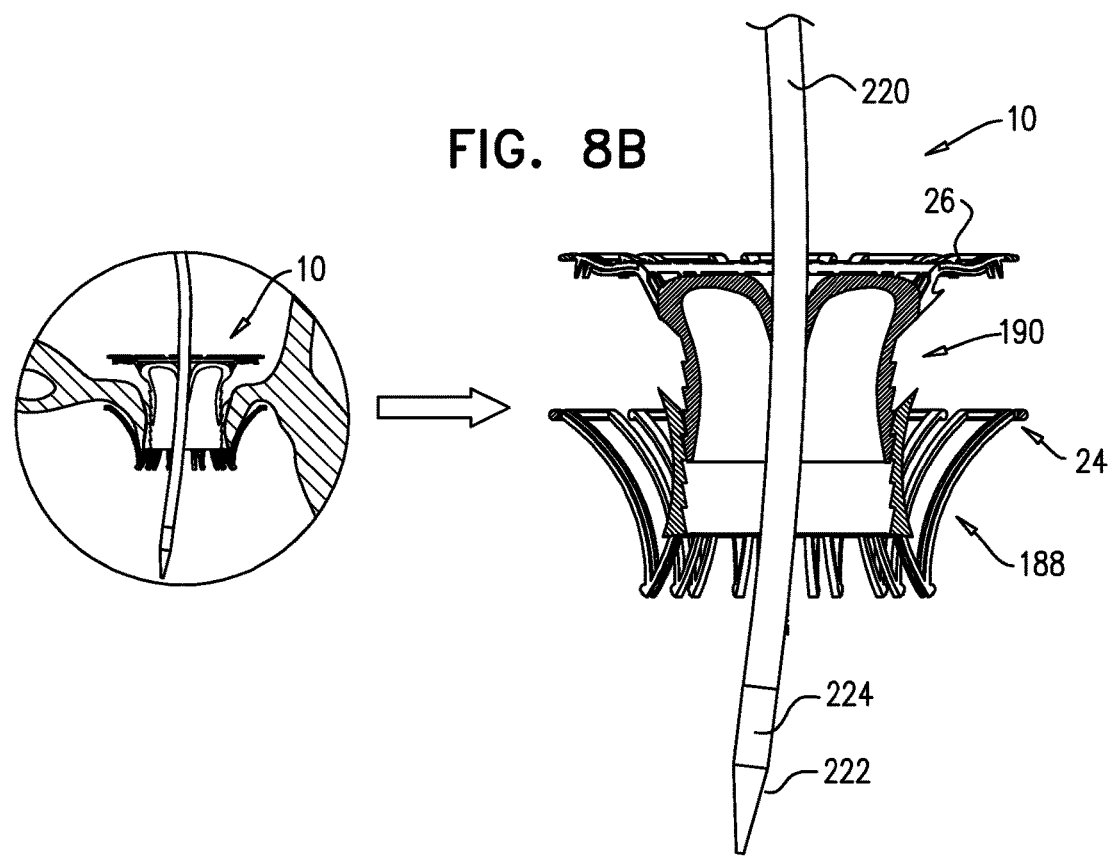

For some applications, a procedure using tool 200 begins with the introduction of catheter 220, as shown in FIG. 8A. Catheter 220 is advanced through the lumen of prosthetic valve 10, until a downstream cap 222 of the catheter passes entirely through the prosthetic valve, as shown in FIG. 8B.

As shown in FIG. 8C, downstream cap 222 is extended downstream from a downstream adaptor holder 224, releasing downstream pulling adaptor 214 from downstream adaptor holder 224. Upon release, downstream pulling adaptor 214 expands. Pulling wire 216 is pulled in an upstream direction, pulling downstream pulling adaptor 214 against downstream portion 188 of downstream skirt 24, as shown in FIG. 8D.

As shown in FIG. 8E, upstream pushing adaptor 212 is deployed from catheter 220 against upstream annular skirt 26. In order to longitudinally contract prosthetic valve 10, the surgeon pulls pulling wire 216 in an upstream direction, while simultaneously pushing on the pushing tube in a downstream direction. The pushing tube pushes upstream pushing adaptor 212 against upstream annular skirt 26, thereby holding the annular skirt against native annulus 32, and holding upstream portion 190 of downstream skirt 24 stationary. Pulling wire 216 pulls on downstream pulling adaptor 214, causing the downstream pulling adaptor to pull downstream portion 188 of downstream skirt 24 toward upstream portion 190, thereby contracting the prosthetic valve.

Upstream pushing adaptor 212 is retracted into catheter 220, and downstream pulling adaptor 214 is retracted into downstream adaptor holder 224, as shown in FIG. 8F. Pulling wire 216 pulls adaptor holder 224 and downstream cap 222 against the body of catheter 220, and the catheter is withdrawn from prosthetic valve 10, as shown in FIG. 8G.

Although prosthetic valve 10 has been described herein as being configured for implantation in and/or at least partial replacement of a native atrioventricular valve, for some applications prosthetic valve 10 is configured for implantation in and/or at least partial replacement of a native aortic valve or a native pulmonary valve, mutatis mutandis.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. A method for use at an atrioventricular valve disposed between an atrium and a ventricle of a heart of a subject, the method comprising:
    transluminally advancing a catheter to the heart;
    via the catheter, advancing to the heart a prosthetic valve including:
        an upstream annular skirt,
        a downstream skirt having a first portion and a second portion, the first portion defining a lumen therethrough, and the second portion defining a plurality of anchoring arms that are coupled to the second portion, and
        a plurality of prosthetic leaflets attached to the first portion and disposed within the lumen;
    expanding the upstream annular skirt in the atrium and expanding the anchoring arms in the ventricle such that the anchoring arms extend radially outward and toward the upstream skirt; and
    subsequently, squeezing tissue of the atrioventricular valve between the upstream annular skirt and the anchoring arms by causing the second portion to slide longitudinally along the outside of the first portion and with respect to the prosthetic leaflets, such that the anchoring arms move longitudinally toward the upstream skirt.

2. The method according to claim 1, wherein expanding the anchoring arms in the ventricle such that the anchoring arms extend radially outward and toward the upstream skirt comprises extending the anchoring arms in the ventricle such that the anchoring arms extend from a downstream portion of the downstream skirt.

3. The method according to claim 2, wherein extending the anchoring arms in the ventricle such that the anchoring arms extend from a downstream portion of the downstream skirt comprises extending the anchoring arms in the ventricle such that the anchoring arms extend from a downstream end of the downstream skirt.

4. The method according to claim 1, wherein causing the second portion to slide longitudinally along the outside of the first portion comprises causing the prosthetic valve to move from an extended, unlocked state into a contracted, locked state.

5. The method according to claim 1, wherein the downstream skirt defines a plurality of ratchet teeth, and causing the second portion to slide longitudinally along the outside of the first portion comprises causing mating between ratchet teeth of the plurality of ratchet teeth.

6. The method according to claim 1, wherein the upstream annular skirt includes a plurality of skirt arms, and expanding the upstream support portion in the atrium comprises expanding the upstream support portion in the atrium such that the plurality of skirt arms extend radially outward.

7. The method according to claim 6, wherein each skirt arm is aligned with a respective one of the anchoring arms, and causing the second portion to slide longitudinally along the outside of the first portion comprises causing each skirt arm to become closer to its respective one of the anchoring arms.

8. The method according to claim 1, wherein causing the second portion to slide longitudinally along the outside of the first portion comprises using a tool to apply (i) an upstream force to the downstream skirt, and (ii) a downstream force to the upstream skirt.

9. The method according to claim 8, further comprising expanding an upstream adapter of the tool, and expanding a downstream adapter of the tool, wherein using a tool to apply the upstream force and the downstream force comprises (i) using the downstream adapter to apply the upstream force to the downstream skirt, and (ii) using the upstream adapter to apply the downstream force to the upstream skirt.

10. The method according to claim 4, wherein the method further comprises, subsequently to expanding the upstream annular skirt in the atrium and expanding the anchoring arms in the ventricle, transluminally advancing the tool to the prosthetic valve.

11. The method according to claim 10, wherein transluminally advancing the tool to the prosthetic valve comprises transluminally advancing the downstream adapter through the lumen of the first portion.

\* \* \* \* \*